(12) United States Patent
Gutwein et al.

(10) Patent No.: US 9,782,328 B2
(45) Date of Patent: Oct. 10, 2017

(54) DEVICES AND METHODS FOR SECURING AN ANTI-LEAK FEEDING TUBE FOR GASTRIC AND/OR INTESTINAL USE

(71) Applicants: UNIVERSITY OF FLORIDA RESEARCH FOUNDATION, INC., Gainesville, FL (US); MEDICAL TOOL AND TECHNOLOGY, LLC, Hawthorne, FL (US)

(72) Inventors: Luke G. Gutwein, Indianapolis, IN (US); Richard D. Helmig, Hawthorne, FL (US)

(73) Assignees: UNIVERSITY OF FLORIDA RESEARCH FOUNDATION, INC., Gainesville, FL (US); MEDICAL TOOL AND TECHNOLOGY, LLC, Hawthorne, FL (US)

( * ) Notice: Subject to any disclaimer, the term of this patent is extended or adjusted under 35 U.S.C. 154(b) by 416 days.

(21) Appl. No.: 14/200,632

(22) Filed: Mar. 7, 2014

(65) Prior Publication Data

US 2014/0276579 A1 Sep. 18, 2014

Related U.S. Application Data

(60) Provisional application No. 61/777,125, filed on Mar. 12, 2013.

(51) Int. Cl.
*A61J 15/00* (2006.01)
*A61M 25/02* (2006.01)

(52) U.S. Cl.
CPC ....... *A61J 15/0061* (2013.01); *A61J 15/0015* (2013.01); *A61J 15/0042* (2013.01); *A61M 25/02* (2013.01); *A61M 2025/0233* (2013.01)

(58) Field of Classification Search
CPC ............ A61M 25/02; A61M 2025/028; A61M 2025/0233; A61B 17/3496;
(Continued)

(56) References Cited

U.S. PATENT DOCUMENTS 4,392,857 A 7/1983 Beran
4,516,968 A 5/1985 Marshall et al.
(Continued)

FOREIGN PATENT DOCUMENTS

JP 2003-038665 2/2003
WO WO 97/25095 7/1997
(Continued)

OTHER PUBLICATIONS

Percutaneous Endoscopic Gastrostomy System product information, [online, webpage, retrieved Apr. 14, 2015] from: https://www.cookmedical.com/data/resources/productReferences/ESC-WM-50146-EN-201206.pdf, pp. 1-2.

*Primary Examiner* — Imani Hayman
*Assistant Examiner* — Brandy S Lee
(74) *Attorney, Agent, or Firm* — Saliwanchik, Lloyd & Eisenschenk

(57) ABSTRACT

Medical device designs for enteral nutrition that inhibit the relative motion of one device member to another device member are herein disclosed. The gastric and/or intestinal feeding tube shaft is disposed of teeth, furrows, ridges, indentions, tabs, or corrugations that operate with an external retaining member. Alternative embodiments utilize an external retaining member with a collet fitting that applies pressure against the gastric and/or intestinal feeding tube shaft. The assemblies prevent the relative motion of the internal retention member relative to the external retaining member and assist in maintaining the internal retention member against the gastric wall.

14 Claims, 21 Drawing Sheets

(58) Field of Classification Search
CPC ........ A61B 2017/3492; A61B 17/3423; A61B 2017/00283; A61B 17/3445; A61B 2017/347; A61B 2090/036; A61J 15/0015; A61J 15/0026; A61J 15/0057; A61J 15/0061; A61J 15/0042

See application file for complete search history.

(56) References Cited

U.S. PATENT DOCUMENTS

| | | |
|---|---|---|
| 4,645,492 A | 2/1987 | Weeks |
| 4,699,616 A | 10/1987 | Nowak et al. |
| 4,834,712 A | 5/1989 | Quinn et al. |
| 4,850,953 A | 7/1989 | Haber et al. |
| 4,861,334 A | 8/1989 | Nawaz |
| 5,073,166 A | 12/1991 | Parks et al. |
| 5,125,909 A | 6/1992 | Heimberger |
| 5,267,968 A | 12/1993 | Russo |
| 5,419,764 A | 5/1995 | Roll |
| 5,458,583 A | 10/1995 | McNeely et al. |
| 5,484,420 A | 1/1996 | Russo |
| 5,860,952 A | 1/1999 | Quinn |
| 5,860,960 A | 1/1999 | Quinn |
| 6,036,673 A | 3/2000 | Quinn |
| 6,042,577 A | 3/2000 | Chu et al. |
| 6,595,971 B1 * | 7/2003 | von Dyck ............... A61F 5/442 604/334 |
| 6,908,454 B2 | 6/2005 | McFarlane |
| 7,238,154 B2 | 7/2007 | Ewers et al. |
| 7,549,200 B2 | 6/2009 | McMichael et al. |
| 7,582,072 B2 | 9/2009 | McMichael |
| 8,241,252 B2 | 8/2012 | Chu et al. |
| 2005/0084327 A1 * | 4/2005 | Chelchowski ........ F16L 19/086 403/345 |
| 2005/0216040 A1 | 9/2005 | Gertner et al. |
| 2005/0251150 A1 | 11/2005 | Hirano |
| 2006/0100604 A1 | 5/2006 | Brenner et al. |
| 2006/0206095 A1 * | 9/2006 | Chu .................... A61J 15/0015 604/539 |
| 2007/0233005 A1 | 10/2007 | McMichael et al. |

FOREIGN PATENT DOCUMENTS

| | | |
|---|---|---|
| WO | WO 00-32260 | 6/2000 |
| WO | WO 02/066108 | 8/2002 |
| WO | WO 03/070151 | 8/2003 |

* cited by examiner

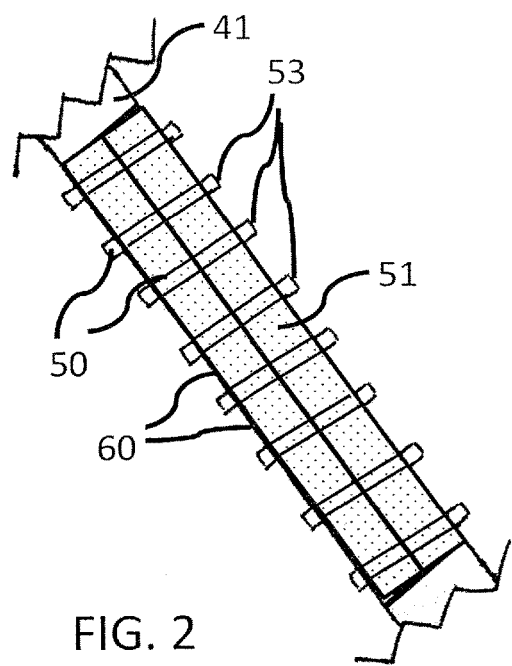
FIG. 2
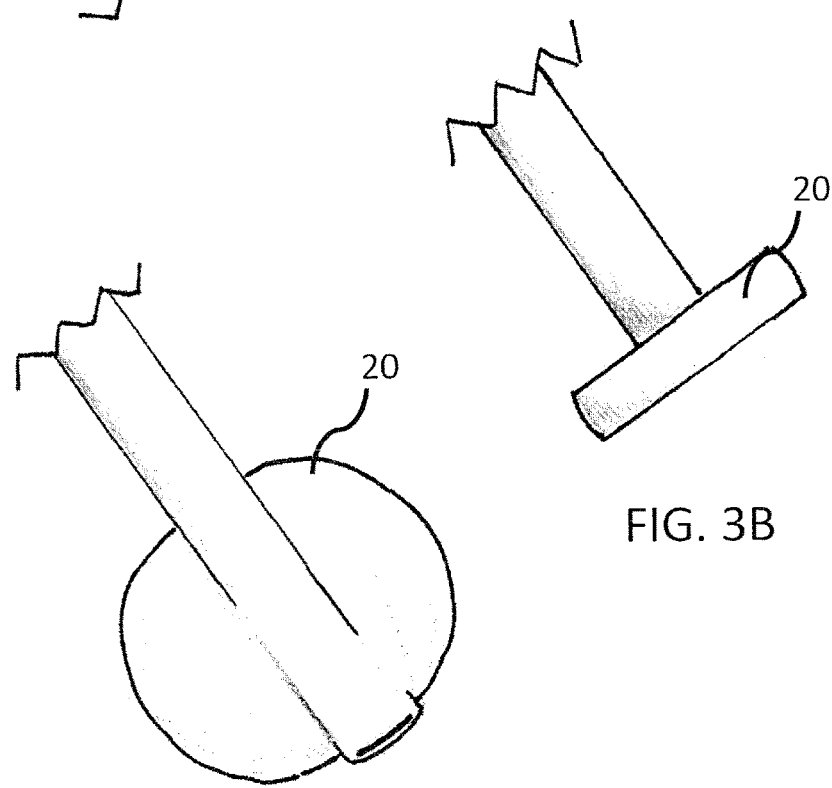
FIG. 3A
FIG. 3B

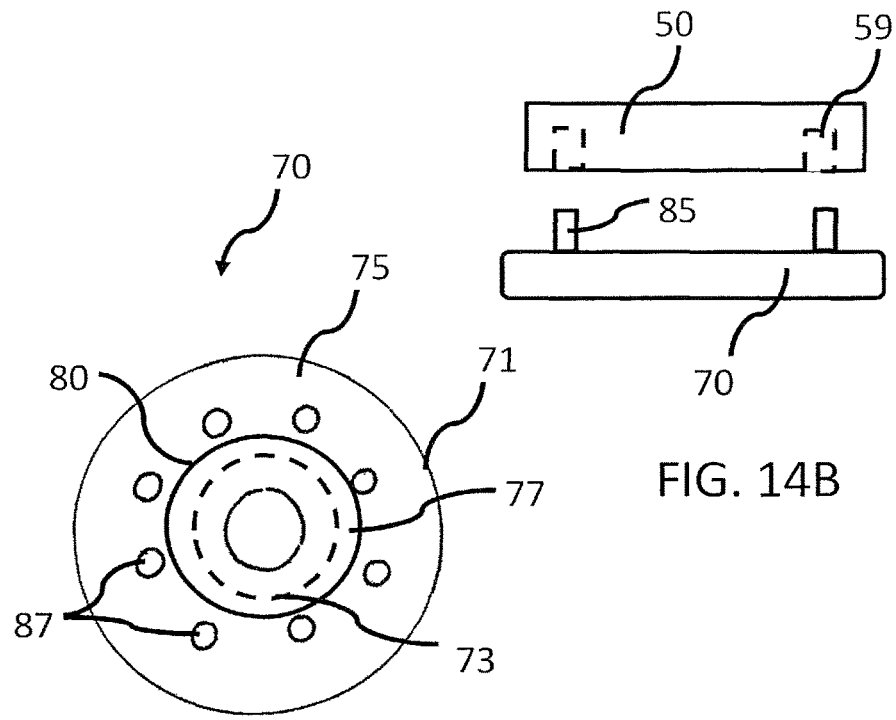
FIG. 14B
FIG. 11
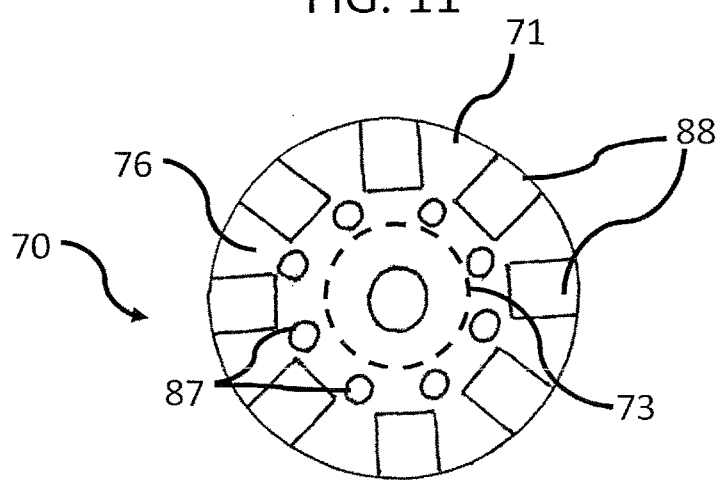
FIG. 12

$F_{net} = F_{applied} - f$ $f = \mu N$

DEVICES AND METHODS FOR SECURING AN ANTI-LEAK FEEDING TUBE FOR GASTRIC AND/OR INTESTINAL USE

CROSS-REFERENCE TO RELATED APPLICATION

The present application claims the benefit of U.S. Provisional Application Ser. No. 61/777,125, filed Mar. 12, 2013, which is hereby incorporated by reference herein in its entirety, including any figures, tables, or drawings.

BACKGROUND OF THE INVENTION

Gastric and enteral tube feeding is commonplace in our healthcare system and plays an important role in supporting nutritional needs for patients unable to ingest food, such as patients suffering from coma, stroke, cancer, and gastrointestinal disorders. Maintenance and care of an enteral feeding tube, particularly a gastrostomy or jejunostomy feeding tube, and the associated stoma site is labor intensive and generates significant healthcare expenditures. Improper feeding tube and stoma care can result in costly emergency department visits, hospital admissions, or even morbidity.

Different methods exist for placing enteral feeding tubes, including surgical, endoscopic, and radiological methods. If placed into the stomach, all three methods result in the gastric wall being juxtaposed to the abdominal wall through a tunneled tract (also referred to as a "fistula"). As an alternative to open surgery, a common method for insertion of a gastrostomy tube is the percutaneous endoscopic gastrostomy (PEG) placement, which is described in detail in U.S. Patent Publication No. 2009/0216186 A1 and U.S. Pat. No. 5,073,166.

Despite the indication, the size required, or the vendor, gastrostomy feeding tubes are manufactured commonly from biocompatible polymers and have an internal retention member (such as, for example, a gastric balloon or bumper) and an external retaining member. In order to prevent leakage of gastric contents from the gastric lumen through the fistula and onto the skin, the internal retention member must be firmly compressed to the gastric opening of the fistula. In the immediate post-placement period, gastric leakage is uncommon for two reasons. The edema or swelling from tissue injury at the placement site causes an initially snug fit between the internal retention member and external retaining member. Secondly, the static coefficient of friction generated by the inner smooth surface of the external retaining member and external smooth polymer surface of the gastrostomy tube is optimized when initially placed because the materials are new. Thus, the combination of post-operative swelling and the optimal frictional force between the device components typically prevents immediate post-operative leakage. It is also common practice during the gastrostomy tube procedure to place a silk suture tightly around the neck portion of an external retaining member to increase the frictional force against the gastric tube, because it is widely recognized that, with time, the static friction between the tube shaft and external retaining member will inevitably be overcome by dynamic friction. The external retaining member can initially be secured to the skin surface with sutures. As swelling reduces and the tube materials wear, the gastrostomy balloon is able to move away from the gastric wall allowing gastric contents to leak out around the gastrostomy tube and onto the skin. Emergency department visits for immediate treatment are prompted when this occurs.

In view of the current problems, there is a need for a gastric feeding tube device that can be easily adjusted to accommodate for changes in the tissues around a fistula and stoma. An exemplary device would have an ergonomic design that is comfortable to wear and easy to place, and that can be utilized no differently than conventional devices. Ideally, such a gastrostomy feeding tube will be adjustable by a healthcare provider or patient without surgical intervention.

BRIEF SUMMARY

The subject invention successfully addresses the above described disadvantages associated with the previously known gastric feeding tubes, particularly with gastrostomy and jejunostomy feeding tubes and provides certain attributes and advantages, which have not been realized by these known devices. In particular, the subject invention provides novel, and highly effective feeding tube devices and methods that provide convenient and effective placement within the body and allow for optimal tube position adjustment and maintenance within a fistula with minimal or no surgical intervention.

Typical gastrostomy and jejunostomy feeding tube devices comprise a polymer tube shaft with an internal retention member at the distal end, such as a balloon or bumper, and one or more ports at or near the proximal end for introduction of feeding materials, medicines, or for inflating an internal retention balloon. An external retaining member around the tube shaft employs frictional force to secure the position of the tube shaft and hold the internal retention device against the gastric wall. The external retaining member can be secured to skin with one or more sutures and, oftentimes, the frictional force can be increased by tying additional suture material tightly around the external retaining member. However, in time, the decrease in tissue swelling and/or material wear can cause the internal retention member to move away from the gastric wall and the tube shaft to slide within the external retaining member.

The embodiments of the subject invention provide gastrostomy and/or jejunostomy feeding tubes (or "feeding tubes") having an external retaining member that can be easily adjusted to effectively maintain a retention member against the gastric wall. One embodiment of the subject invention utilizes a tube shaft with multiple flexible or semi-flexible external structures, such as, for example, annular or semi-annular corrugations, ridges, ribs, tabs, flanges, or the like, generally referred to herein as "teeth," such that there are "furrows" or indentations, between the teeth, along the length of a feeding tube, which can engage with an external retaining member. An external retaining member can have an internal space that cooperatively engages with the one or more teeth and/or furrows, causing it to be retained in place relative to the tube shaft.

In another embodiment, an external retainer member is modified with a male connector having a wedge shape capable of forming a compression fit with an internally shouldered female nut. With this embodiment, the external retaining member can be located at any position on a feeding tube. The female shouldered nut can then be operably connected to the male connector, which is compressed around the tubing to maintain the position of the external retaining member.

Typically, an external retaining member is placed adjacent to the skin around a stoma. Once an external retaining member is cooperatively engaged with a tube shaft of the subject invention, at an initial placement site, relative motion of the tube shaft between the external retaining member and the internal retention member is inhibited within a fistula. In an exemplary embodiment, the position of an external retaining member of the subject invention can be manually adjusted at any time by a healthcare provider or a patient to control the pressure applied to the skin by the external retaining member, and the force applied to the gastric wall by an internal retention member, and prevent leaking gastric contents.

A conceivable complication may be gastric wall/skin ischemia if the feeding tube is manually adjusted too forcefully. However, the feeding tube embodiments of the subject invention should be placed no differently than conventional feeding tubes. Thus, it should not be positioned any tighter than the present standard of care. The embodiments of the subject invention are as safe as currently used feeding tubes and can minimize complications associated with leaking gastric contents. The embodiments disclosed herein can demonstrate reduced peri-stomal wound complications, homecare visits, emergency department visits, hospital admissions, and surgery for complications. In addition, the durable designs also promote longevity to the devices. There is potential for significant healthcare cost savings.

Other aspects and further scope of applicability of the present invention will become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 2 is a partial view of an embodiment of a feeding tube having affixed thereto one embodiment of a toothed sleeve.

FIGS. 3A and 3B are partial views of embodiments of feeding tubes according to the subject invention. FIG. 3A shows an example of an internal retention member balloon structure on the distal end of a gastrostomy feeding tube. FIG. 3B shows an example of an internal retention member bumper structure on the distal end of a gastrostomy feeding tube.

FIG. 4A shows an embodiment of a sleeve as a unitary structure that can be wrapped around a tube shaft. FIG. 4B illustrates an embodiment of a toothed sleeve comprising two sections that can be affixed to a tube shaft.

FIG. 8A is an axial cross-sectional view showing a tooth having a circumferential shape having multiple straight edges. FIG. 8B is an axial cross-sectional view showing a tooth having a circumferential shape that is oval.

FIG. 11 is a top plan view of an embodiment of an external retaining member according to the subject invention.

FIG. 12 is a bottom plan view of an embodiment of an external retaining member according to the subject invention.

FIG. 14B is a front elevation view of an embodiment of an external retaining member having external members that can engage with a tooth having compatible openings therein.

DETAILED DISCLOSURE

Figure 1:
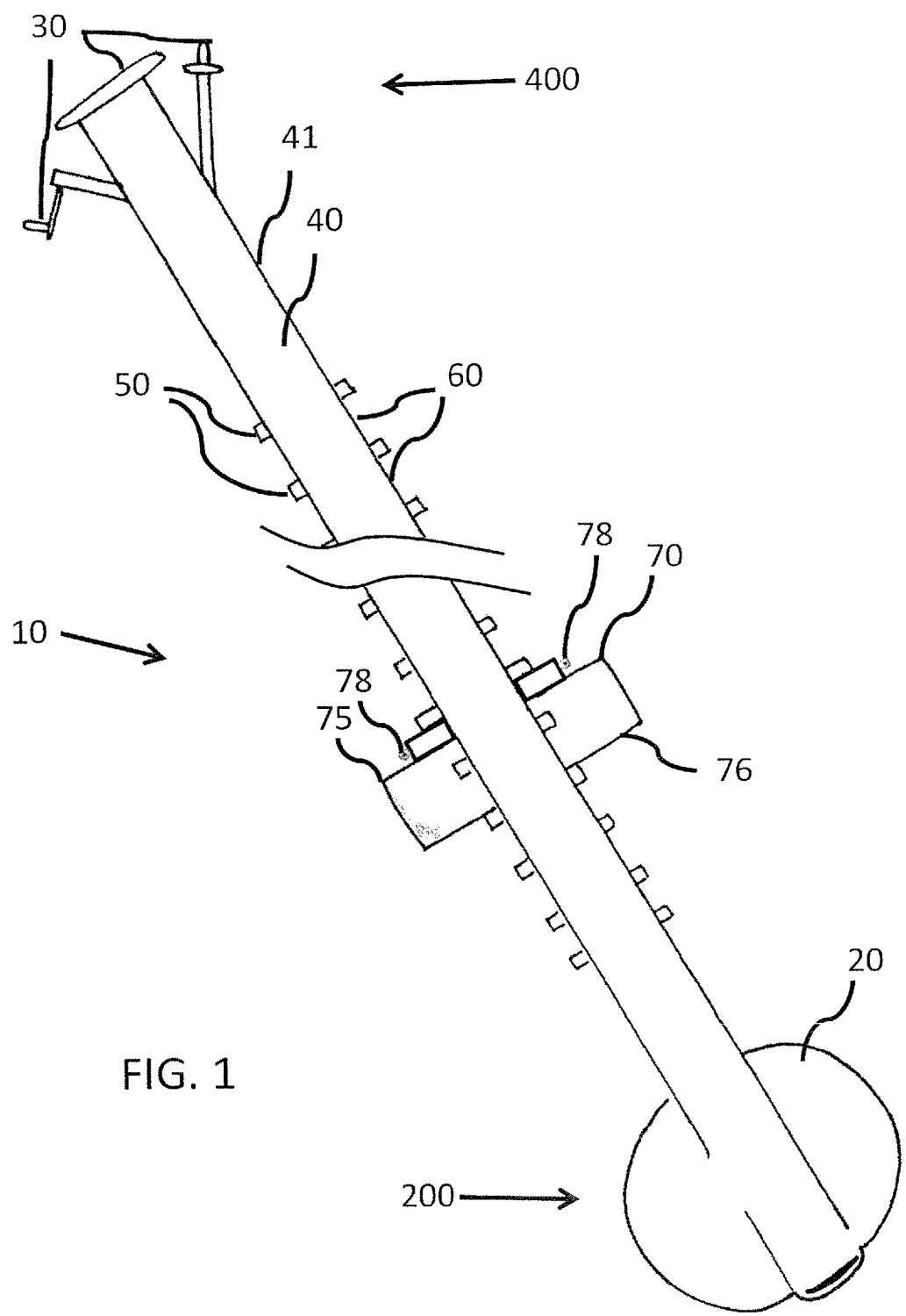
FIG. 1 is front elevation view of an embodiment of a feeding tube according to the subject invention.

The subject invention describes embodiments of gastric and enteral feeding tubes. More specifically, the subject invention provides one or more embodiment(s) of gastrostomy and jejunostomy feeding tubes, or similarly used devices, capable of providing nutrition and other substances directly into the stomach or intestines through a fistula in the body.

The following description will disclose that the subject invention is particularly useful in the field of gastric feeding, in particular, devices used for delivering nutrition and other substances to the stomach or intestine. However, a person with skill in the art will be able to recognize numerous other uses that would be applicable to the devices and methods of the subject invention. While the subject application describes, and many of the terms herein relate to, a use for gastrostomy and jejunostomy feeding, other modifications and uses apparent to a person with skill in the art and having benefit of the subject disclosure are contemplated to be within the scope of the present invention.

In the description that follows, a number of terms used in enteral feeding, particularly gastrostomy or jejunostomy feeding devices and methods are utilized. In order to provide a clear and consistent understanding of the specification and claims, including the scope to be given such terms, the following definitions are provided.

As used herein, the terms "individual" and "patient" are used interchangeably to refer to any species in the animal kingdom, preferably vertebrates, and more preferably mammals, such as humans. Such individuals or patients can range in age from neonates to elderly.

The term "health care provider" is also used in the subject invention merely for literary convenience. The term can include highly trained surgeons, physicians, nurses or individuals trained to provide limited care to an individual or patient. Thus, the term should not be construed as limiting in any way. The devices, apparatuses, methods, techniques and/or procedures of the subject invention could be utilized by any person desiring or needing to do so and having the necessary skill and understanding of the invention.

The term "gastric feeding tube" and "gastric tube" are used interchangeably and for literary convenience throughout the application. The embodiments of the subject invention are particularly useful for gastric feeding into the stomach. However, additional placement may occur at a variety of anatomical locations, which would utilize other types of feeding tubes, including, but not limited to gastrostomy, percutaneous endoscopic gastrostomy, gastro-jejunostomy, or jejunostomy feeding tubes. Thus, these terms should not be construed as limiting the invention to any particular type of enteral or gastric feeding tube.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

Finally, reference is made throughout the application to the "proximal end" and "distal end." As used herein, the proximal end is that end of a gastric tube that can be disposed in vivo, such as within a stomach, intestine, or other internal digestive space, or that end on which an internal retention member is located. Conversely, the distal end of a gastric tube is that end disposed ex vivo, or that end having one or more ports and which can be engaged with an external retaining member.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the subject invention, it can be seen that the subject invention generally comprises a gastric feeding tube 10 having a proximal end 200 and a distal end 400 with conventional gastric feeding tube features, including an internal retention member 20 on the proximal end and one or more ports 30 on the distal end. Between the proximal and distal ends, is a tube shaft 40. Certain embodiments include multiple teeth 50 and furrows 60 that can be cooperatively engaged with an external retaining member 70 disposed thereon. Other embodiments comprise a colletted external retaining member 100 that, when coupled with a union nut 150, creates a frictional force capable of gripping to a feeding tube. With this embodiment, an external retaining member can be securely placed at any of an infinite number of locations on the length of the tube.

Figure 5:
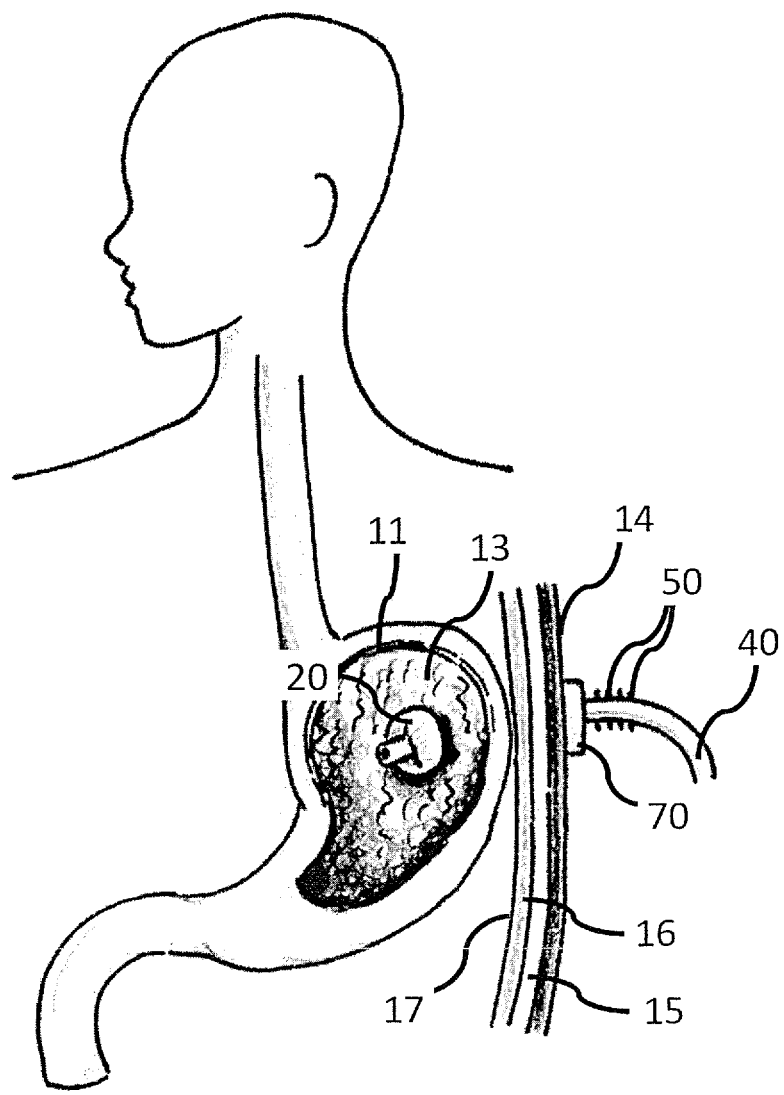
FIG. 5 is an anatomical coronal sectional in situ view of an embodiment of a furrowed gastrostomy feeding tube according to the subject invention. It can be seen that an embodiment of the subject invention can pass through the abdominal wall skin, the subcutaneous tissue (fat), muscle, and peritoneum to enter the lumen of the stomach.
Figure 20:
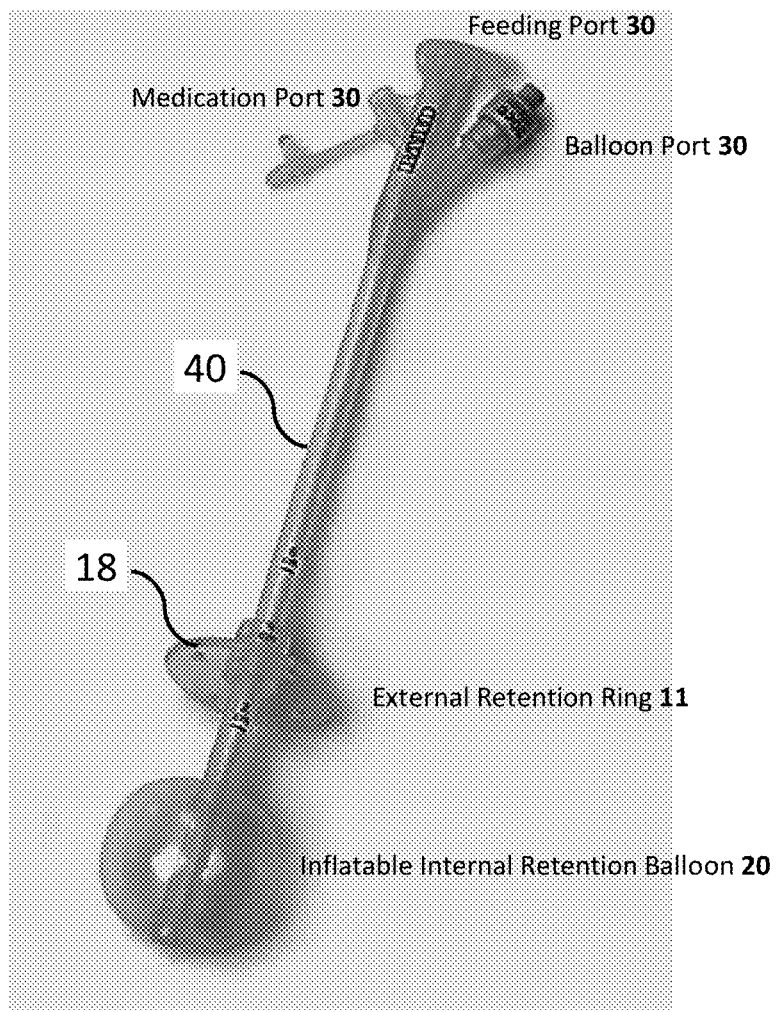
FIG. 20 is a photograph of a conventional gastrostomy feeding tube with a smooth tube shaft
Figure 21:
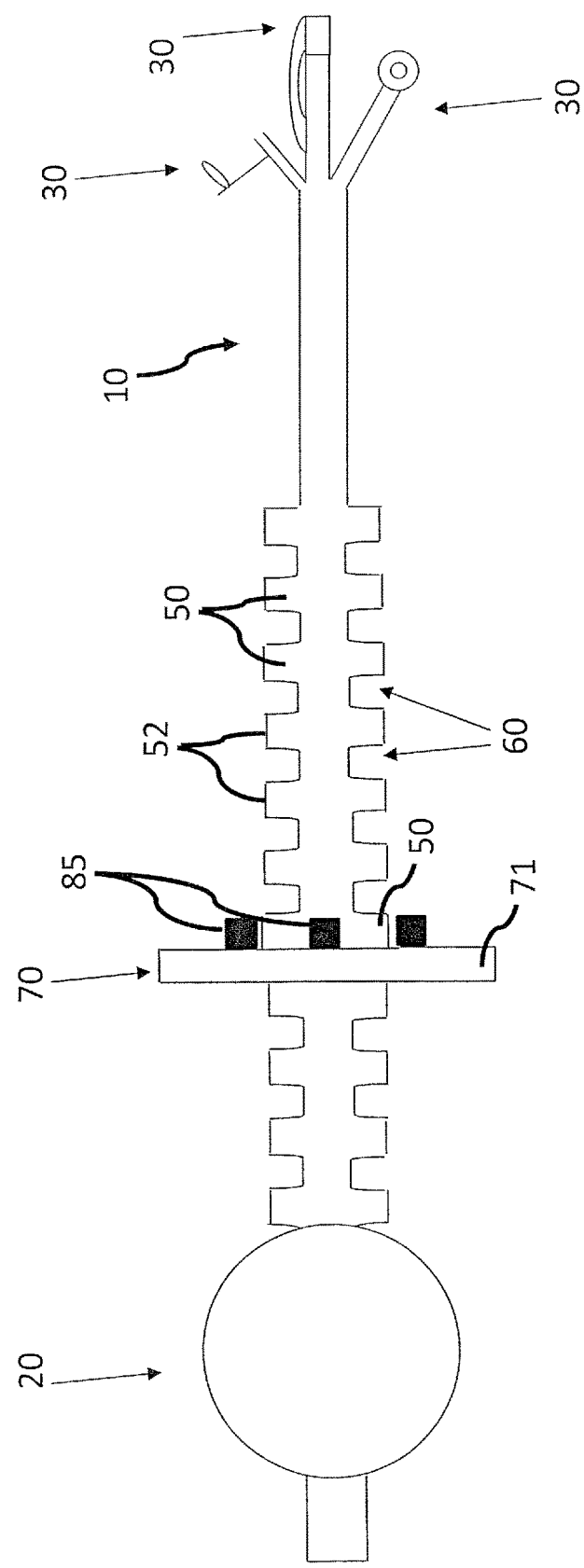
FIG. 21 is a front elevation view of an embodiment of a gastrostomy feeding tube with teeth and furrows on the tube shaft according to the subject invention.

FIG. 1 illustrates an embodiment of a gastric feeding tube 10 according to the subject invention. In FIG. 5 it can be seen that a gastric feeding tube can pass through the abdominal wall skin 14, subcutaneous tissue (fat) 15, muscle 16, peritoneum 17, and gastric wall 11, entering the lumen of the stomach 13. Commercially available gastric feeding tubes are available in a myriad of configurations with different features. Configurations can comprise one or more of a proximal feeding port, a medication port, and a balloon port, examples of which are shown in FIGS. 1, 20, and 21. Additionally they can include different types of internal retention members, including, but not limited to, balloons, bumpers, rings, and similarly used features, non-limiting examples of which are shown in FIGS. 1, 3A, 3B, 20, and 21. If the internal retention member is a ring or bumper rather than an inflatable balloon then a balloon port may not be present. Additionally, a medication port might not be present. Thus, it should be understood that the embodiments of the subject invention can be incorporated and utilized with feeding tubes having any of a variety of internal retention members 20 and/or ports 30.

Figure 18:
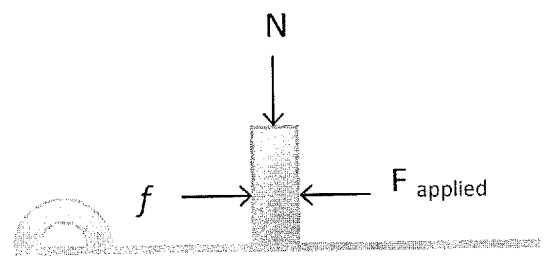
FIG. 18 is a hemi-sectional view of a conventional gastrostomy feeding tube illustrating by a force diagram the forces typically exerted on a feeding tube, where, f is the frictional force between the feeding tube shaft and the external retaining member, N is the normal force exerted by the external retaining member onto the feeding tube shaft, μ is the coefficient of friction, $F_{applied}$ is the force applied to the external retaining member, and $F_{net}$ is the net force.
Figure 19:
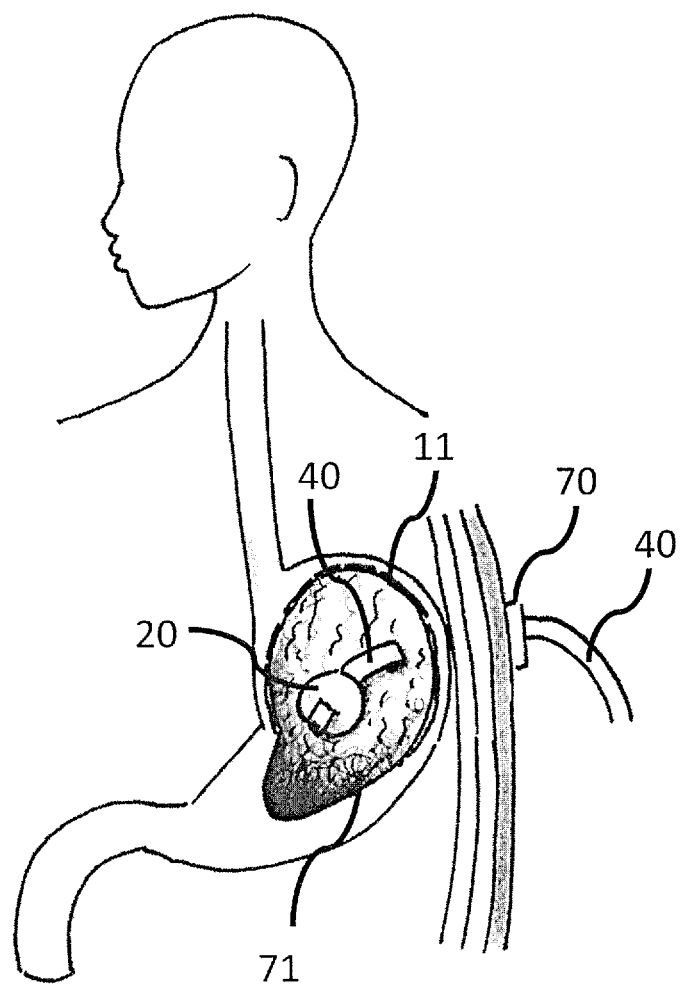
FIG. 19 is an anatomical coronal sectional view showing a conventional gastrostomy feeding tube that is no longer juxtaposed to the gastric wall.

The combination of post-operative swelling and optimal static frictional force usually prevents immediate post-operative leakage. FIG. 18 illustrates that frictional force, f, is equal to the static coefficient of friction, µ, (inherent material property) multiplied by N which is the normal force between the external retention ring and the gastrostomy tube. It is common practice during a gastrostomy tube procedure to tie a silk suture tightly around the external retention ring collar to increase N, the normal force, because it is widely recognized that with time and normal reduction of post-operative swelling, static friction will inevitably be overcome by dynamic friction. This is due to the gastrostomy tube sliding inward at the external retention ring surface where it contacts with the feeding tube shaft. Regardless of whether the external retention ring is fixed to the skin with suture, the gastrostomy balloon is still susceptible to moving away from the gastric wall, as illustrated in FIG. 19, allowing gastric contents to leak out around the gastrostomy tube and onto the skin.

In one embodiment of the subject invention, a tube shaft 40 comprises multiple teeth 50 arranged on at least a portion of the exterior surface 41 of the tube shaft. As will be discussed in detail, the teeth cooperatively engage with an external retaining member 70, one embodiment of which is illustrated in FIG. 5. Ideally, the configuration and/or arrangement of the teeth on a tube shaft 40, when cooperatively engaged, will allow an external retaining member 70 to provide a consistent, reliable pressure to the area around the tube shaft. This interaction between the teeth and the external retaining member will also augment the frictional force to enhance the ability of the internal retention member 20 to maintain its abutment against the gastric wall, preventing leakage of gastric contents. However, the teeth should also be configured and have sufficient flexibility that the external retaining member can be moved proximally 200 or distally 400, as needed, to adjust to changes in the surrounding tissues and control leakage from the fistula.

Figure 6A:
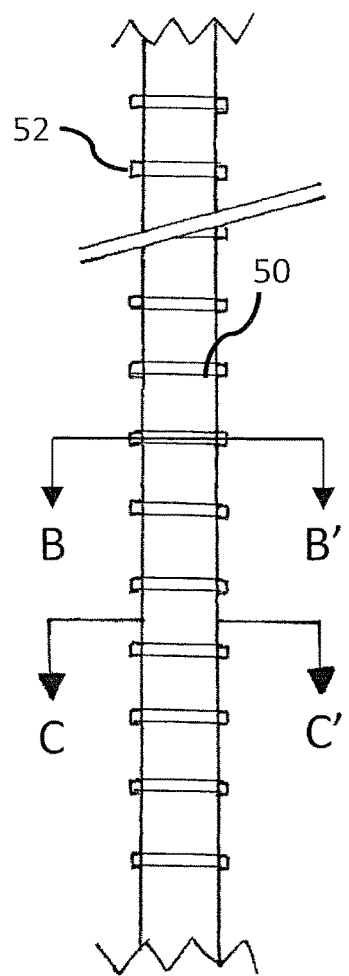
FIG. 6A shows an embodiment of a furrowed tube shaft according to the subject invention. Line B-B' shows the location of the cross-sectional view shown in FIG. 6B and line C-C' shows the location of the cross-sectional view shown in FIG. 6D.
Figure 6B:
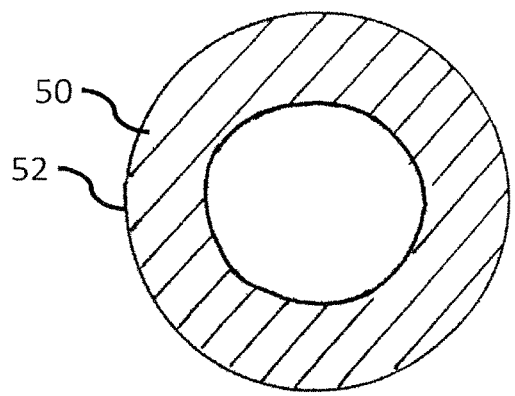
FIG. 6B is an axial cross-sectional view of an embodiment taken along line B-B' in FIG. 6A, which goes through an annular tooth on a tube shaft according to the subject invention. Additional lumens may be present.
Figure 6D:
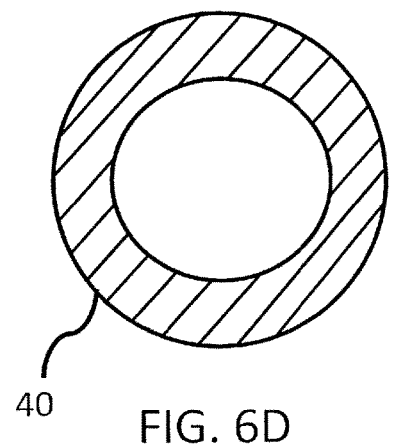
FIG. 6D is an axial cross-sectional view of an embodiment taken along line C-C' in FIG. 6A, which goes through a tube shaft at an indentation or furrow, according to the subject invention. Additional lumens may be present.
Figure 6C:
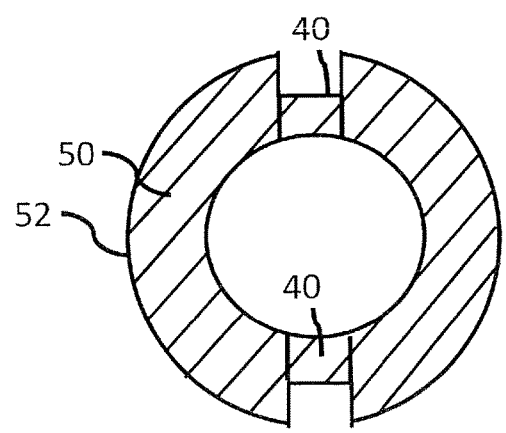
FIG. 6C is an axial cross-section view of an alternative embodiment, also taken along line B-B' in FIG. 6A, which goes through a semi-annular tooth on a tube shaft, according to the subject invention. Additional lumens may be present.

In one embodiment, the teeth 50 are comprised of annular rings that encircle the tube shaft. FIGS. 1, 6A, 6B, 9A, and 21 illustrate non-limiting examples of this embodiment. In an alternative embodiment, the teeth are semi-annular rings that encircle the tube shaft. FIGS. 2 and 6C illustrate a non-limiting example of this alternative embodiment. The number of teeth utilized can depend upon any of a variety of factors that would be known to a person skilled in the art. Preferably, there will be a sufficient number of teeth with optimally spaced furrows 60 between them that the tube shaft and an internal retention member 20 can be precisely positioned distally or proximally relative to the external retaining member. It can also be preferable for the number of teeth and the furrows between them to be such that an external retaining member 70 can be adjusted in sufficiently small increments on a tube shaft, so as to obtain the optimal tension between an internal retention member 20 and the gastric wall 13. In a further embodiment, the teeth allow an external retaining member to be moved in both the distal and proximal directions, as necessary. Thus, the teeth can secure the position of an external retaining member, but also allow it to be moved if necessary. Ideally, the number and size of the teeth are such that an external retaining member can be engaged without over-adjusting or under-adjusting against a stoma and surrounding skin.

In one embodiment, the teeth are formed as part of the tube shaft 40, such that they are contiguous with the external surface 41. Thus, a tube shaft could be manufactured with teeth on one or more preferred areas of the external surface. In one embodiment, teeth are formed along most, or all, of the tube shaft that can be external to a stoma. In an alternative embodiment, teeth are formed on only a portion of the tube shaft that can be external to a stoma. More specifically, teeth are formed on about 1 inch to about 4 inches of the tube shaft that would be closest to the stoma, perhaps even located within a fistula. Gastrostomy feeding tubes are available in several lengths depending upon the size of the patient. It would be within the skill of a person trained in the art to determine the appropriate number and proper location of teeth on a tube shaft, or how much of the length of a tube shaft requires teeth. Such variations which perform the same function, in substantially the same way, with substantially the same result are within the scope of the subject invention.

Alternatively, the teeth 50 can be structures that are fixedly attached to a tube shaft, either individually or in groups. In one embodiment, a conventional gastric tube is configured with multiple teeth in one or more locations, as described in the preceding paragraph. The teeth can be fixedly attached by any of a variety of techniques and devices known in the art. By way of non-limiting example, the teeth can be heat-sealed or sonically-sealed to the exterior surface. By way of another non-limiting example, the teeth can be fixedly attached with an adhesive product. In another embodiment, the teeth can be removable for repair or modification.

Figures 4A, 4B:
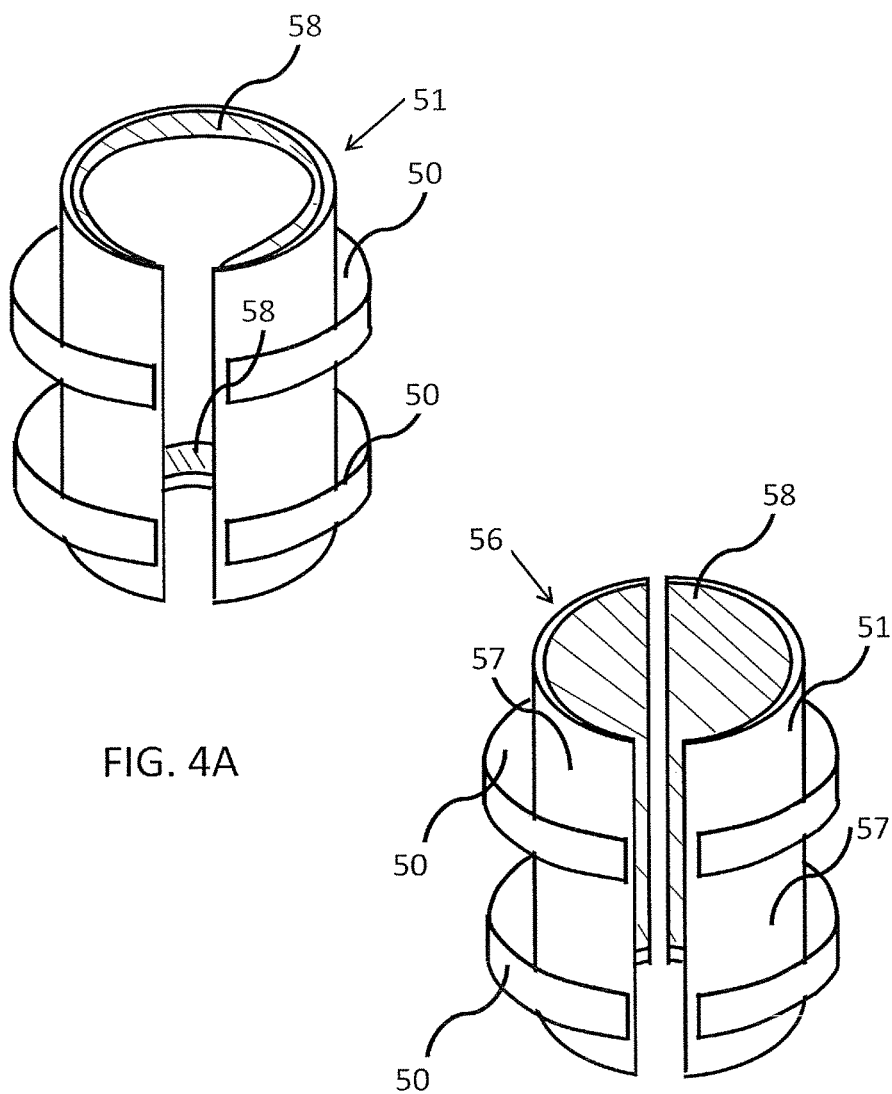
FIGS. 4A and 4B are front perspective views of alternative embodiments of a toothed sleeve.

Alternatively, the teeth 50 can be fixedly attached to, or otherwise incorporated with, a sleeve 51 that can be attached to a conventional gastrostomy feeding tube shaft 40. A sleeve can be of any desirable length and can be positioned in any desirable location on a tube shaft. FIG. 2 illustrates one embodiment of a sleeve, according to the subject invention, that has been wrapped around a tube shaft. In a further embodiment, multiple sleeve portions 56 having a few teeth thereon can be utilized to create customized lengths on a tube shaft. Sleeve portions can be placed end-to-end on a tube shaft to create any desired length of toothed tube shaft. FIGS. 4A and 4B illustrate examples of sleeve portions 56 that can be combined on a tube shaft to create a custom length of toothed tube shaft. In an alternative embodiment, the sleeve is divided into two or more sleeve sections 57 that can be individually attached to a tube shaft. With this embodiment, a sleeve can be divided into two or more sections that can be aligned on a tube shaft. FIG. 4B illustrates one example of sleeve sections 57 that can be combined to create a toothed tube shaft.

A sleeve can be affixed to a tube shaft so that it can cooperatively engage with an external retaining member 70. In one embodiment, a sleeve has an interior adhesive surface 58 that allows it to be fixedly attached to a tube shaft. FIG. 4B illustrates an embodiment having an interior adhesive surface 58. In an alternative embodiment, a sleeve has a surface that is partially adhesive, such that only a portion of the sleeve, such as, for example, the distal and proximal ends, can be fixedly attached to the exterior surface 41 of a tube shaft, such as shown, for example, in FIG. 4A In a further embodiment, a interior adhesive surface allows the sleeve to be removable from a tube shaft. Thus, the sleeve can be removed when desired for modification or replacement. A person with skill in the art would be able to determine any number of devices and methods by which a sleeve can be affixed, removably or permanently, to a tube shaft. Such variations, which perform the same function, in substantially the same way, to achieve substantially the same result, are within the scope of the subject invention.

The placement of a sleeve 51 can be important, since it typically will cooperatively engage with an external retaining member 70. Therefore, manipulation of the sleeve should be performed with as much care and accuracy as possible to ensure proper alignment. To facilitate this, the sleeve can be configured to make it easier to place it on a tube shaft. In one embodiment, the sleeve to which the teeth are attached comprises a semi-rigid material that is formed into a generally tubular shape, such as shown in the examples in FIGS. 4A and 4B. This allows the sleeve to be placed around a tube shaft and properly aligned before adhering it to the tube shaft. Alternatively, the sleeve can comprise a flat sheet of material that can be wrapped around a tube shaft. In still another alternative embodiment, a sleeve section 57 can comprise a semi-rigid material with a portion of a tooth thereon. Two or more sleeve sections can be affixed to a tube shaft with the teeth portions aligned so that they can cooperatively engage with an external retaining member.

An external retaining member 70 can be utilized to cooperatively engage with one or more teeth 50, so as to exert force to maintain an internal retention member 20 against the gastric wall 11 of an individual. In one embodiment, an external retaining member 70 has a plate-member 71, comprising a topside 75, facing generally towards the distal end 400 of the tube shaft and a bottom side 76, facing generally towards the proximal side 200 of the tube shaft. A plate-member 71 can have any preferred circumferential shape and/or diameter. In a specific embodiment, an external retaining member has a generally circular circumferential shape. In a further embodiment, the external retaining member has a diameter of between approximately 3.0 cm and approximately 6.0 cm. In a more particular embodiment, an external retaining member has a diameter of between approximately 4.0 cm. and 5.0 cm. The thickness of an external retaining member can also vary depending upon a variety of factors that are understood by a person skilled in the art. In one embodiment, the external retaining member has a thickness between approximately 2.0 mm and approximately 5.0 mm. In a more particular embodiment, an external retaining member has a thickness between approximately 2.5 mm and approximately 3.5 mm.

In a further embodiment, the plate-member has a channel 72 therethrough, from the top side to the bottom side, non-limiting examples of which are shown in FIGS. 7, 11, 12 and 17. The channel can be positioned anywhere within the plate-member. In a particular embodiment, the channel is located generally in the center of the plate member. In an alternative embodiment, the channel is offset from the center of the plate. In a still further embodiment, there is more than one channel within a plate-member, such that the external retaining member can be disposed on a tube shaft in the most advantageous position.

In use, the teeth on a tube shaft of the subject invention will traverse the channel when the external retaining member is adjusted on a tube shaft of the subject invention. Therefore, it can be important that the choice of dimensions of the channel and the material of the external retaining member and/or teeth be carefully considered. A person with skill in the art can determine the appropriate channel dimensions and materials to utilize for an external retaining member. Such variations which allow the embodiments of the invention to function as described herein are within the scope of the subject invention.

The teeth on a tube shaft can have any of a variety of shapes and dimensions that are conducive to being operatively engaged with an external retaining member. The shape of the teeth can depend upon a variety of factors, including, but not limited to, the type of materials utilized, the location and number of teeth, the configuration of an external retaining member to be employed with the teeth, and other factors. In one embodiment, the teeth are disk-like structures encircling a tube shaft, such that they form multiple annular shoulders between the proximal 200 and distal 400 ends of a tube shaft. The teeth can be contiguous structures, such that each is completely annular and surrounds a tube shaft, such as shown, for example in FIG. 6B. Alternatively, the teeth can be non-contiguous, such that each one does not completely surround, or intermittently surrounds a tube shaft, i.e., they are semi-annular, such as shown, for example, in FIG. 6C. In another embodiment, both contiguous and non-contiguous teeth can be utilized on the same tube shaft. The teeth can be fixedly attached to the tube shaft exterior 41 directly or they can be indirectly attached, such as with a sleeve 51, described above. Further, the teeth can extend generally perpendicular from a tube shaft to terminate in a peripheral edge 52. An advantage of the embodiments described herein is the ability of the external retaining member to move both distally and proximally on a tube shaft. Therefore, it can be beneficial for the shape of the teeth to facilitate this duality of motion. It is within the skill of a person trained in the art to determine any of a variety of shaped teeth according to the subject invention. It should be understood that such variations which perform in the same manner, in substantially in the same way, with substantially the same result are within the scope of the subject invention.

Figures 9A, 9B, 9C:
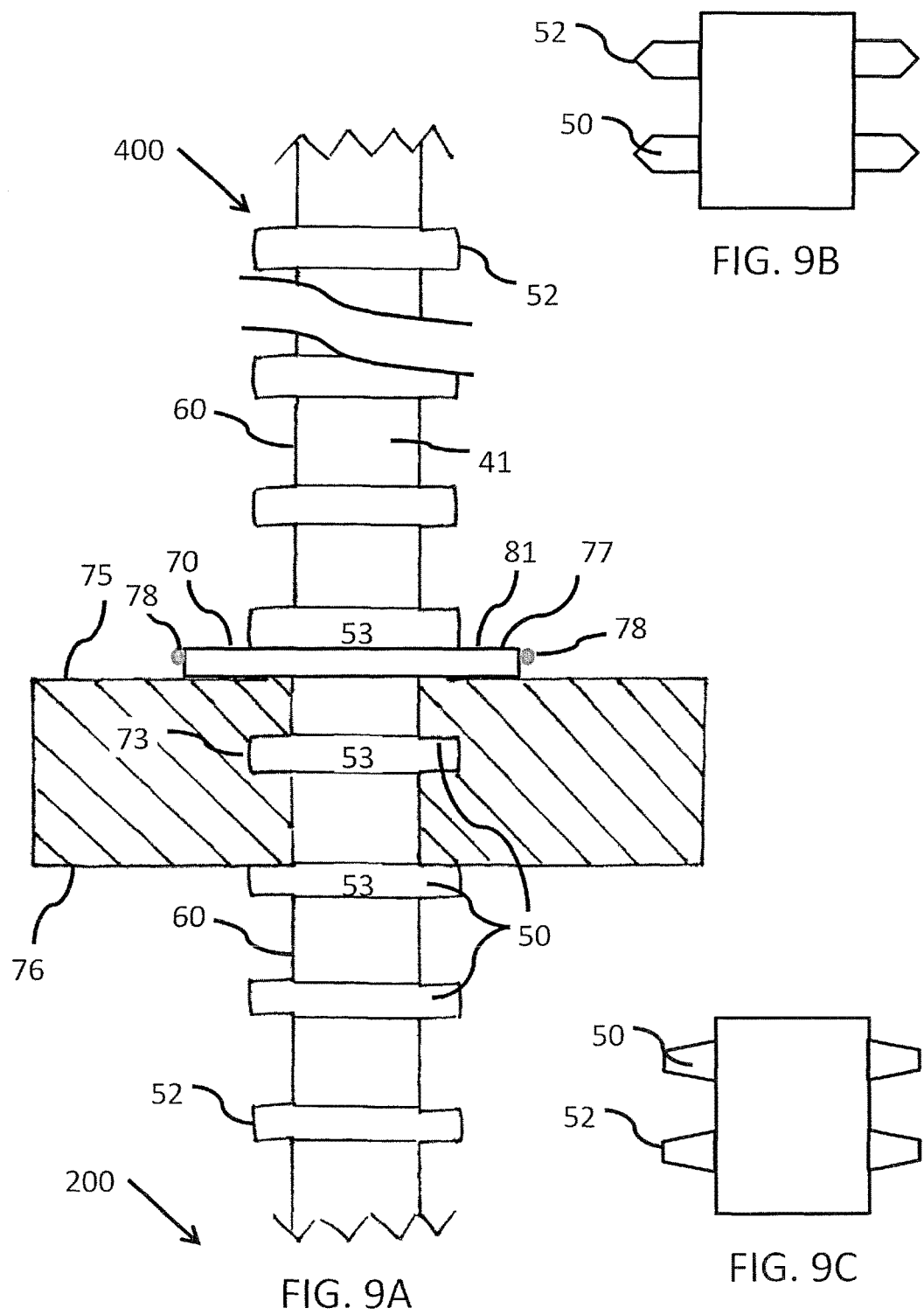
FIG. 9A is a longitudinal cross-sectional view of an embodiment of an external retaining member disposed onto an embodiment of a tube shaft according to the present invention.
FIGS. 9B and 9C illustrate alternative embodiments of tooth configurations.

In one embodiment, the teeth have a consistent thickness, from where they extend from a tube shaft to a peripheral edge 52, giving them an essentially washer-shape 53 appearance. FIGS. 2 and 9A illustrate one example of such an embodiment, wherein the peripheral edge is generally a blunt, flat edge, such as shown, for example, in FIG. 9C. In an alternative embodiment, the teeth taper towards the peripheral edge. In a particular embodiment, the teeth have a frustoconical shape 54, when viewed in cross-section, such that the peripheral edge 52 of a tooth is narrower than where it extends from a tube shaft, and ends in a blunt, flat edge. In another particular embodiment, the teeth have a fin-shape 55, when viewed in cross-section, so that they have a peripheral edge 52 that is narrower than where they extend from a tube shaft and taper to a fine peripheral edge or point, such as shown, for example, in FIG. 9B.

Figure 8A:
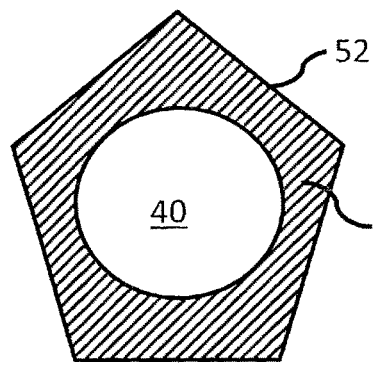
FIGS. 8A and 8B illustrate embodiments of teeth according to the subject invention.
Figure 8B:
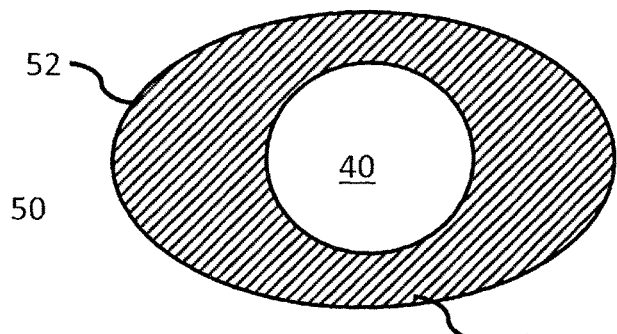

In a further embodiment, the teeth can have a circumferential shape that is conducive to engaging with an external retaining member 70 and/or a collar 77, as will be discussed below. It can also be beneficial if the teeth have a circumferential shape that inhibits rotation of an external retaining member on the feeding tube. In one embodiment, the teeth have a circumferential shape that engages with an external retaining member and/or collar to inhibit rotation of the external retaining member. In a further embodiment, the teeth have a circumferential shape that inhibits rotation, such as, for example, triangular, square, oval, some other non-circular shape, or any other polygonal shape capable of reducing rotation when engaged with an external retaining member or collar, as discussed below. FIGS. 8A and 8B illustrate alternative embodiments of teeth 50 having non-rotating circumferential shapes.

A typical gastric feeding tube 10 includes an external retention ring 18, such as shown on FIG. 20. Because of the internal retention member 20 at the proximal end and the various ports that are attached to the distal end, it is usually not possible to remove the external retaining ring from a gastric tube. As mentioned previously, an external retention ring often experiences a loss in static frictional force, which causes it to slide undesirably on the tube shaft. However, utilization of a sleeve 51 on a gastric tube shaft 40 can advantageously provide additional friction force to prevent an external retention ring from sliding. Usually the material of an external retention ring 18 is flexible enough that the ring can be forced over the teeth 50 on a sleeve 51, of the subject invention. Also, for such uses, the teeth on a sleeve can be made with a smaller diameter, so that they are more conducive for use with an existing external retention ring.

An external retaining member 70 can have one or more structures that cooperatively engage with one or more teeth 50 on a tube shaft 20. The structures should have sufficient tolerance therebetween that they engage securely with one or more teeth, such that the external retaining member is maintained at a preferred position on a tube shaft with minimal rocking, shifting or other undesirable movement therebetween. However, such structures should also engage with one or more teeth, so that they allow the external retaining member to be moved distally or proximally along the length of the tube shaft, as described above. Also as described above, the teeth on a tube shaft can be arranged to cooperatively engage with an external retaining member 70, holding it in an optimal location and minimizing unnecessary movement.

Figure 7:
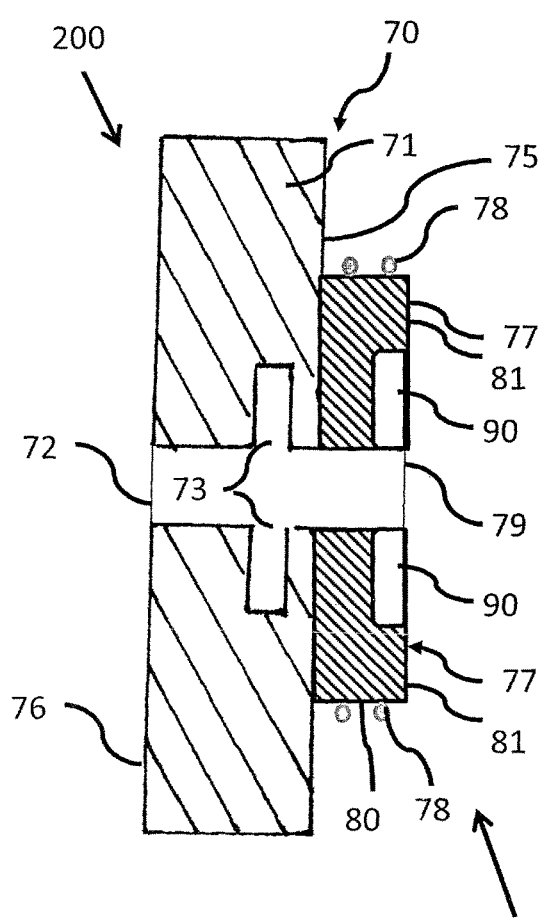
FIG. 7 is a longitudinal cross-sectional view of an embodiment of an external retaining member according to the subject invention.
Figure 17:
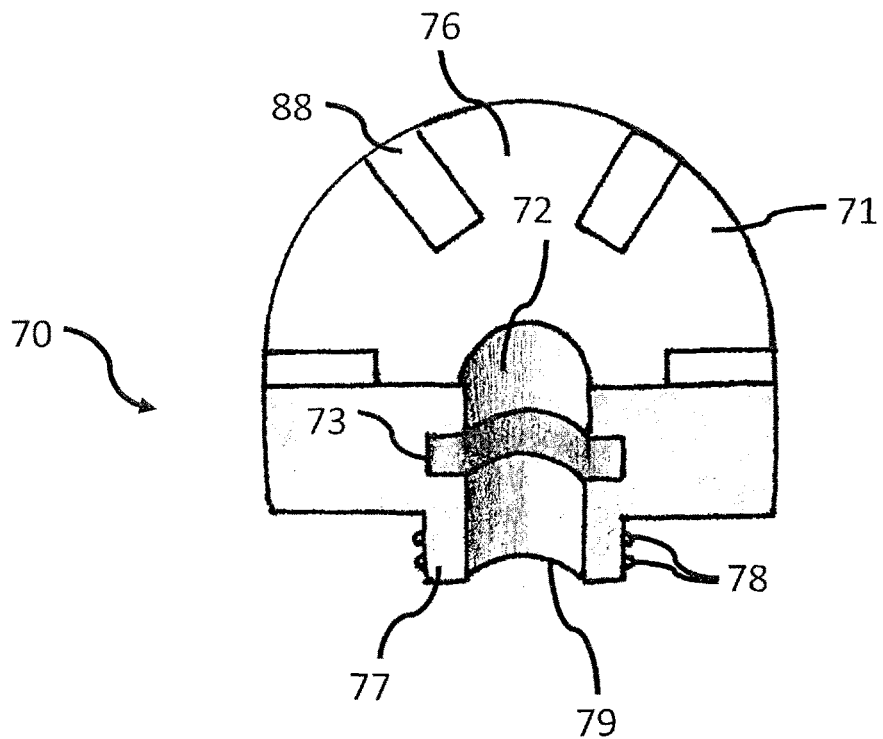
FIG. 17 is a hemi-sectional perspective view of an embodiment of an external retaining member according to the subject invention.

In one embodiment, the channel 72 of an external retaining member comprises a cavity 73 having a shape and dimensions that allow it to cooperatively engage with at least one tooth on a tube shaft. The cavity can be contiguous with the channel, so that as the tube shaft is moved within the channel to an optimal location, one or more teeth on the tube shaft can slide through the channel and at the desired location can be cooperatively engaged with the cavity. In one embodiment, a cavity is a space within the channel that has a larger diameter than the channel. FIGS. 7, 9A, and 17 illustrate examples of this embodiment. In a further embodiment, the cavity 73 has a shape and dimensions that allow it to engage with one or more teeth when an external retaining member 70 is moved in either a proximal or distal direction. In one embodiment, the teeth are temporarily deformed or changed in shape as they move through the channel. When they encounter the cavity 73, they expand or reform to their original shape, causing them to operably engage with the cavity. An external retaining member 70 can have more than one cavity 73. In one embodiment, two or more cavities each engage with a tooth on a tube shaft. In a further embodiment, each of the two or more cavities can engage with different teeth simultaneously or one tooth can be engaged with either one of the cavities, such that only one tooth is retained within the external retaining member at a time. In an alternative embodiment, an external retaining member 70 has a single cavity 73 that can engage with more than one tooth at a time on a tube shaft, such that more than one tooth is retained within the external retaining member at a time.

In a particular embodiment, an external retaining member has a cavity 73 that is contiguous with a channel 72 within an external retaining member 70. In a further embodiment, the shape and dimensions of a cavity are such that it can be operatively engaged with one or more annular or semi-annular teeth on a tube shaft. In one embodiment, a cavity is shaped to be operatively engaged with particularly shaped teeth, such as described above. In an alternative embodiment, an external retaining member has a cavity 73 with a more generalized shaped that can be operatively engaged with teeth having any of a variety of shapes or dimensions. FIG. 7 illustrates one example of a cavity 73 having a shape that can be complementary to a washer-shaped tooth, but could also be operatively engaged with teeth having a cross-sectional shape that is frustoconical or even a fin-shaped tooth.

The cooperative engagement of one or more teeth 50 with the cavity 73 disposed within an external retaining member advantageously provides a healthcare worker or patient an ability to adjust the length of the feeding shaft between the internal retention member 20 and the external retaining member 70. Thus, when the internal retention member moves away from the gastric wall 11, as shown, for example, in FIG. 19, the external retaining member 70 can be adjusted to a more proximal location on the tube shaft. This shortens the length of the tube shaft between the external retaining member and the internal retention member, which draws the internal retention member closer to the gastric wall, reestablishing or strengthening the anti-leak properties therebetween. Likewise, if the internal retention member applies too much force against the skin and gastric wall, the external retaining member can be moved distally on the tube shaft. Thus, the cooperative engagement with one or more teeth can hold the external retaining member in an optimal location on the tube shaft.

It can also be beneficial if the external retaining member can cooperatively engage with more than one tooth. As mentioned above, the internal cavity 73 can be variously configured to engage with more than one tooth. There can also be more than one internal cavity 73, such that each one can be cooperatively engaged with one or more teeth. However, in an alternative embodiment of the external retaining member, one or more external surfaces of the external retaining member 70 can operatively engage with one or more teeth. The external surfaces can contact one or more teeth or they can form some operative connection that aids in holding the external retaining member in place on a tube shaft.

Figure 10:
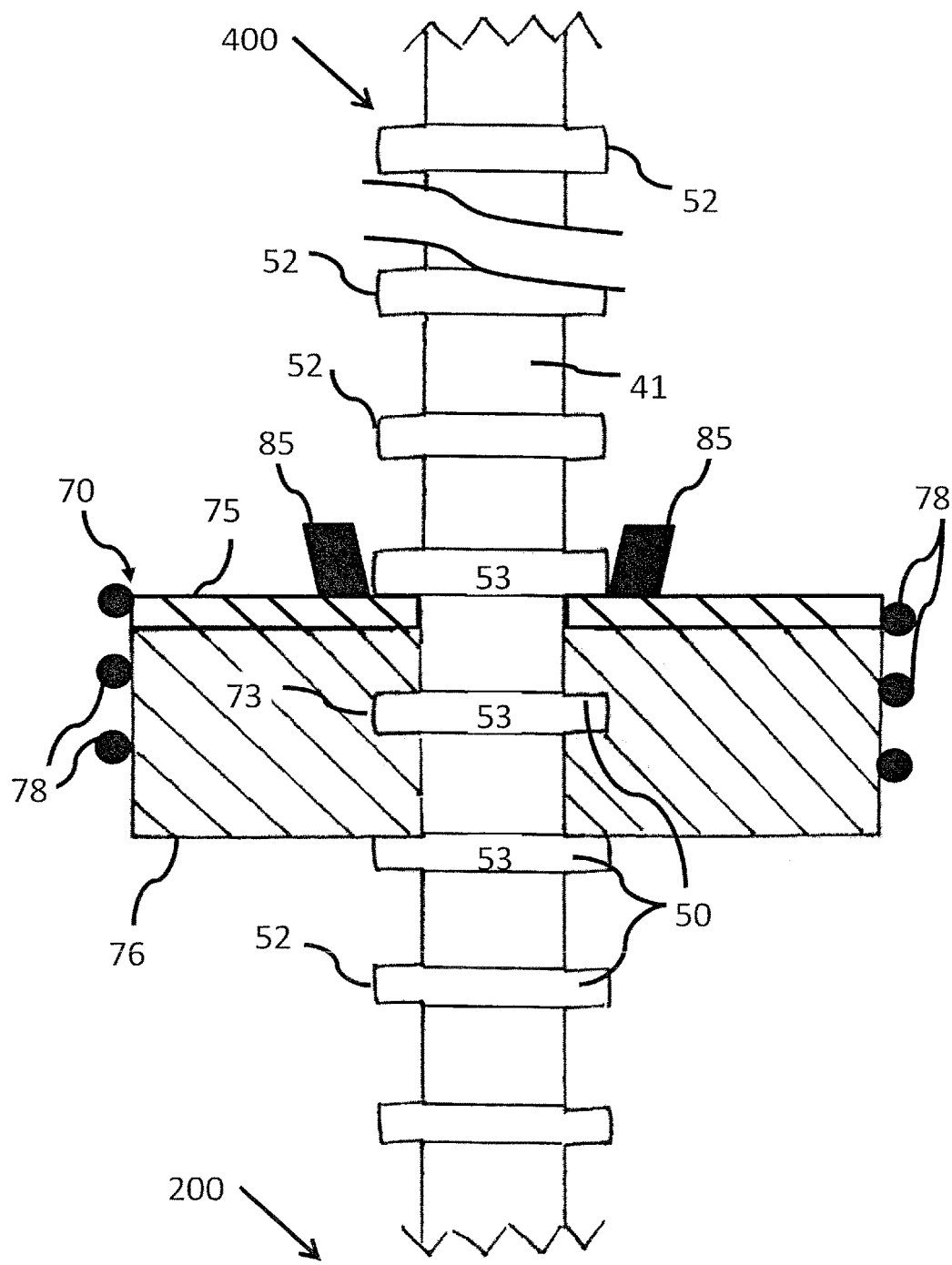
FIG. 10 is a longitudinal cross-sectional view of an alternative embodiment of an external retaining member disposed onto an embodiment of a tube shaft according to the present invention.

In one embodiment, the external retaining member has dimensions that allow a top side 75, facing generally in the distal 400 direction and/or a bottom side 76, facing generally in the proximal 200 direction, to abut against teeth that are adjacent thereto. This can necessitate the teeth on a tube shaft being spaced at a particular distance so that they can abut against one or more external surfaces. With this embodiment, a cavity 73 within an external retaining member 70 can be cooperatively engaged with one or more teeth 50, which will simultaneously cause a top side 75 to abut against the proximal side of another more distal tooth on the tube shaft. The bottom side 76 can also simultaneously abut against the distal side of a more proximal tooth. A non-limiting example of this embodiment is illustrated in FIG. 10, which shows a single internal cavity 73 engaged with a tooth on a tube shaft and adjacent distal and proximal teeth abutting against the top side 75 and bottom side 76, respectively, of an external retaining member. In a further embodiment, an external surface of an external retaining member can have one or more of various ergonomic structures 78 that can assist in adjustment of the external retaining member on a tube shaft. Such ergonomic structures 78, such as shown, for example, in FIG. 10, can facilitate grasping of the external retaining member during adjustment.

One advantage of the embodiments of the subject invention is the ability of the external retaining member to be utilized without sutures. The engagement of the external retaining member with one or more teeth on a tube shaft ensures that the feeding tube 10 will remain at the proper, position and tension. Thus, the use of sutures to secure the external retaining member 70 to the skin may not be required.

The use of sutures can also prevent standard external retaining rings 18, as shown in FIG. 20, from rotating on a tube shaft. It can also be beneficial if embodiments of the external retaining member of the subject invention do not rotate on the shaft. Rotation about the shaft can cause wear on the tube and friction against the skin, which can be uncomfortable to a patient.

Figure 15:
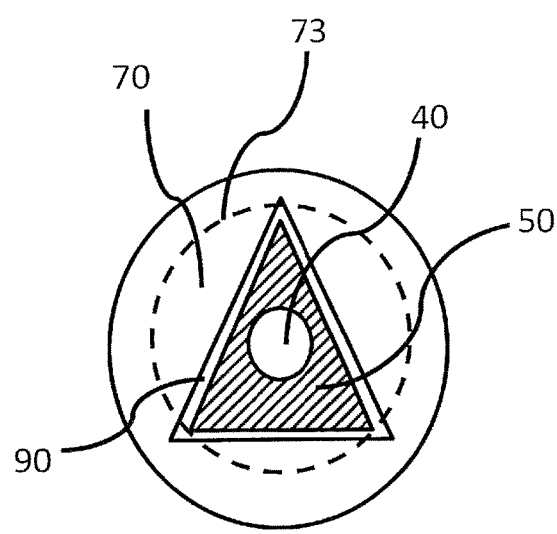
FIG. 15 is a top plan view of the alternative embodiment in FIG. 14A having a tooth on tube shaft disposed within a depression in the external retaining member.
Figure 14A:
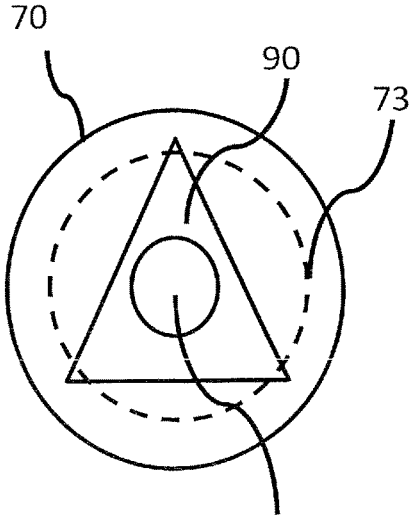
FIG. 14A is a top plan view of an alternative embodiment of an external retaining member showing a depression from receiving a tooth on a tooth shaft.

To inhibit such rotation, an external retaining member can have one or more features on an external surface that can engage with teeth on a tube shaft. In one embodiment, an external retaining member 70 has a depression 90 around the channel 72 that is complementary to and can accommodate the shape of a tooth; ideally a tooth with a non-circular circumferential shape. The depression can have a sufficient depth so that a first tooth 50 fixedly attached to a tube shaft 40 can be disposed within a cavity 73 within the external retaining member and a second tooth can be simultaneously mated with the depression and essentially seat into it sufficiently to inhibit rotation of the tooth and, hence, the tube shaft. FIG. 14A is a distal end view of one embodiment of an external retaining member 70 having a depression 90 therein and around the channel 72. FIG. 15 is another distal end view illustrating an example of a tooth 50 on a tube shaft 40 that is seated into a depression 90 on an external retaining member.

Figure 16:
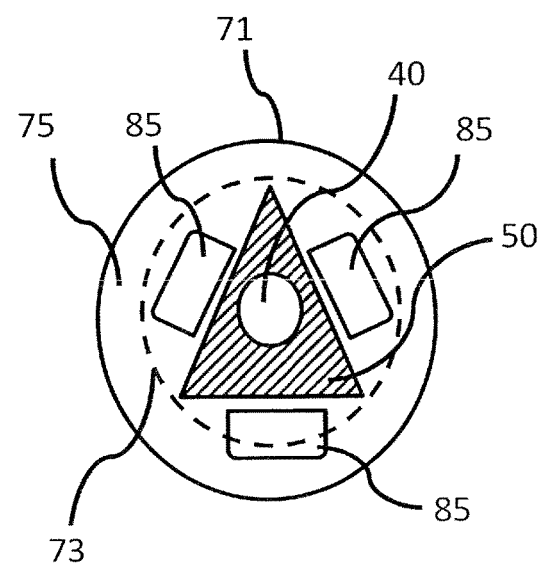
FIG. 16 is a top plan view of a external retaining member having multiple external members for engaging with a tooth on tube shaft.

In an alternative embodiment, an external retaining member can have one or more external members 85 that engage with a tooth on a tube shaft; ideally a tooth with a non-circular circumferential shape. The external members can extend above the top side 75 of an external retaining member and can be positioned so that they engage with the circumferential shape of a tooth to inhibit rotation. As with the above embodiment, the external members can have a sufficient height above the top side 75 that a first tooth 50 fixedly attached to a tube shaft 40 can be disposed within a cavity 73 within the external retaining member 70 and a second tooth can be simultaneously aligned with the external members 85 and essentially seated between the external members components, so that they sufficiently inhibit rotation of the tooth and, hence, the tube shaft. FIG. 16 is a distal end view of an embodiment of an external retaining member and FIG. 21 is a front elevation view another embodiment, each illustrating embodiments of an external retaining member 70 having multiple external members 85 that can engage with a tooth.

In an alternative embodiment, the external members can engage with cavities, cut-outs, or other types of compatible openings 59 within a tooth. In still another alternative, the external member can have one or more openings that engage with external members, or the equivalent thereof, on a tooth. For example, an external member 85 can fit into a compatible opening 59 in the proximal side of a tooth, similar to a peg-in-hole arrangement, which can inhibit rotation of the tooth. This embodiment would be particularly advantageous for use with teeth having a circular circumferential shape, but could be utilized with any tooth configuration. FIG. 14B illustrates one example of this embodiment.

There are a variety of configurations that can be determined by a person skilled in the art for minimizing or eliminating rotation of a tooth relative to an external retaining member. It should be understood that such variations or modifications, which provide the same function, in substantially the same way, with substantially the same result, are within the scope of the subject invention.

Conventional gastric feeding tubes usually include a collar around which a suture is often tightened to increase the frictional force with the tube shaft 40. Embodiments of the subject invention can also employ a collar as an abutment against one or more adjacent teeth to assist in holding the external retaining member in place on a tube shaft and inhibit proximal and/or distal sliding. In one embodiment, the top side 75 of an external retaining member has a fixedly attached collar 77 that can abut against a tooth. FIGS. 7, 9A, and 17 illustrate embodiments of external retaining members 70 having an attached collar 77. Collar embodiments can have circumferential shapes that are, for example, oval, square, triangular, rectangular, or any other polygonal shape. A collar can also have various ergonomic structures 78 that can assist in adjustment of the collar on a tube shaft. FIGS.

7 and 9A illustrate examples of collars with ergonomic structures 78 that can be grasped when adjusting the external retaining member. A collar can also have features that engage with a tooth on a tube shaft, as described above for an external retaining member. Such features as external members 85 and depressions 90, described above, are equally applicable for use with a collar, and such features are reiterated here with respect to the use of collars. FIG. 7 illustrates an embodiment of a collar with ergonomic structures 78 in the form of ribs or ridges on an outer edge 80 that can be used to grasp the collar for making adjustments. Other embodiments can include various shapes of depressions that can cooperatively engage with the teeth on a tube shaft. FIG. 7 illustrates a non-limiting example of a collar having an upper surface 81 with a depression 90 that can be cooperatively engaged with a tooth 50 having a compatible, ideally non-circular, circumferential shape, as described above.

The dimensions of a collar can vary depending upon one or more various factors, such as, but not limited to, materials utilized, diameter of the teeth, distance between the teeth, and other factors that are known to a person skilled in the art. In one embodiment, a collar extends from the topside 75 of an external retaining member between approximately 0.5 cm and 1.5 cm. In a more particular embodiment, a collar extends from the topside 75 between approximately 0.75 cm and approximately 1.25 cm. In a specific embodiment, a collar extends from the topside 75 approximately 1.0 cm.

In a further embodiment, a collar has an aperture 79, contiguous with the channel 72 in an external retaining member, through which a tube shaft and teeth thereon can slide therethrough, non-limiting examples of which are shown in FIGS. 11 and 17. The aperture can be located anywhere within a collar. In a particular embodiment, the aperture is located generally in the center of a collar. In an alternative embodiment, the aperture is offset from the center of a collar. In use, the teeth on a tube shaft of the subject invention traverse the channel when the external retaining member is adjusted. Therefore, it can be important that the dimensions selected for the aperture and the material of the collar be carefully considered. A person with skill in the art can determine the appropriate channel dimensions and materials to utilize, so that a furrowed tube shaft can pass through a channel 72 and an aperture 79 of an external retaining member. Such variations which allow the embodiments of the invention to function as described herein are within the scope of the subject invention.

In one embodiment, a collar 77 is a separate component that juxtaposes with the external retaining member and encircles a tube shaft. With this embodiment, a collar can be a singular structure having any of various sizes and shapes that are capable of operatively engaging with one or more teeth, as described above. FIGS. 9A and 11 show embodiments of a separate collar that has a washer-like shape, being a flat disk-like member.

In a further embodiment, the collar comprises a material or has structural components that make it more rigid than an external retaining member. This can be beneficial if the material of the external retaining member comprises a material that is pliable, soft, conforming, or is otherwise more comfortable against the skin of a patient. The collar, juxtaposed with the external retaining member, can comprise material that is more rigid, so that it can provide strength to apply force against the less rigid external retaining member to inhibit leaking.

Figure 13:
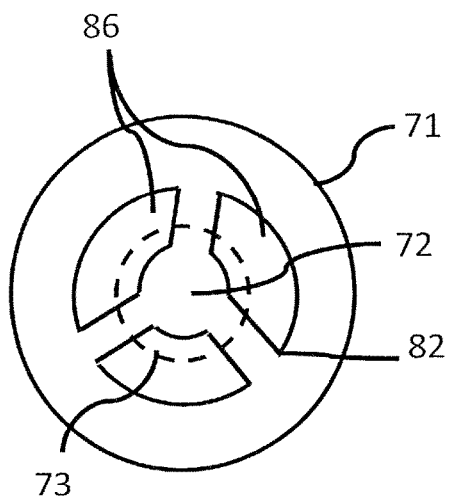
FIG. 13 is a top plan view of an alternative embodiment of an external retaining member according to the subject invention. This embodiment specifically illustrates a collar comprising multiple sections.

In an alternative embodiment, a collar is fixedly attached to, or is otherwise contiguous with, an external retaining member. FIG. 17 illustrates an embodiment of a collar that is part of an external retaining member. With this embodiment, a collar can abut against one or more teeth, as described above, to assist in holding the external retaining member in place on a tube shaft to inhibit proximal and/or distal sliding. In another embodiment, the collar comprises sections 86 that are formed as part of the external retaining member. The sections can be of any size or shape, so long as they are capable of engaging with one or more teeth on a tube shaft. FIG. 13 illustrates one example of a collar comprising multiple sections 86. In one embodiment, the collar comprises tabs or ridges that extend above the channel 72 to engage with one or more teeth. In a specific embodiment, the sections 86 form grooves 82 that can cooperatively engage with a tooth. FIG. 13 illustrates an example of a collar comprising different types of multiple sections around a channel 72, which form grooves 82.

An alternative embodiment of the subject invention utilizes a "collet fitting" to secure an external retaining member to a gastric tube. Collets are well-known in the art and typically comprise a male connector in the form of a slotted sleeve with two or more arm sections and are commonly used to hold circular or rod-like pieces. The male connector often comprises a wedge shape designed to abut against an inclined plane within a threaded female nut. As the nut is screwed down onto the collet, the inclined plane within the nut encounters the wedge-shape of the collet, forcing the arm sections of the collet to press against a tube or rod within the sleeve. The amount of force applied to the tube or rod in the collet is directly proportional to the amount of force applied by the nut to the collet. The use of collets in mechanical and machine operations is well known. A disadvantage of utilizing these devices is the ease with which they can be easily over-tightened making them difficult, or even impossible to release, or worse damaging a device therein.

Advantageously, embodiments of the subject invention provide a modified collet and union nut that can be utilized on a tube shaft 40 that inhibit damage or undesirable constriction of the tube shaft 40. In one embodiment, the external retaining member is modified to incorporate one or more securing elements that can be cooperatively engaged with one or more cooperating features in or on the union nut. In one embodiment, an external retaining member is modified to have continuous threading, as a securing element, and a collet encircling the channel 72. This colletted external retaining member 100 can be operably engaged with embodiments of a union nut 150 that also has continuous threading, as a cooperating feature, compatible with the continuous threading on the colletted external retaining member 100, and an internal inclined plane 156. When the union nut 150 is operably engaged with the colletted external retaining member 100, by means of their respective continuous threading, it forces the collet against the tube shaft of a gastric tube disposed within the channel 72.

Figure 22:
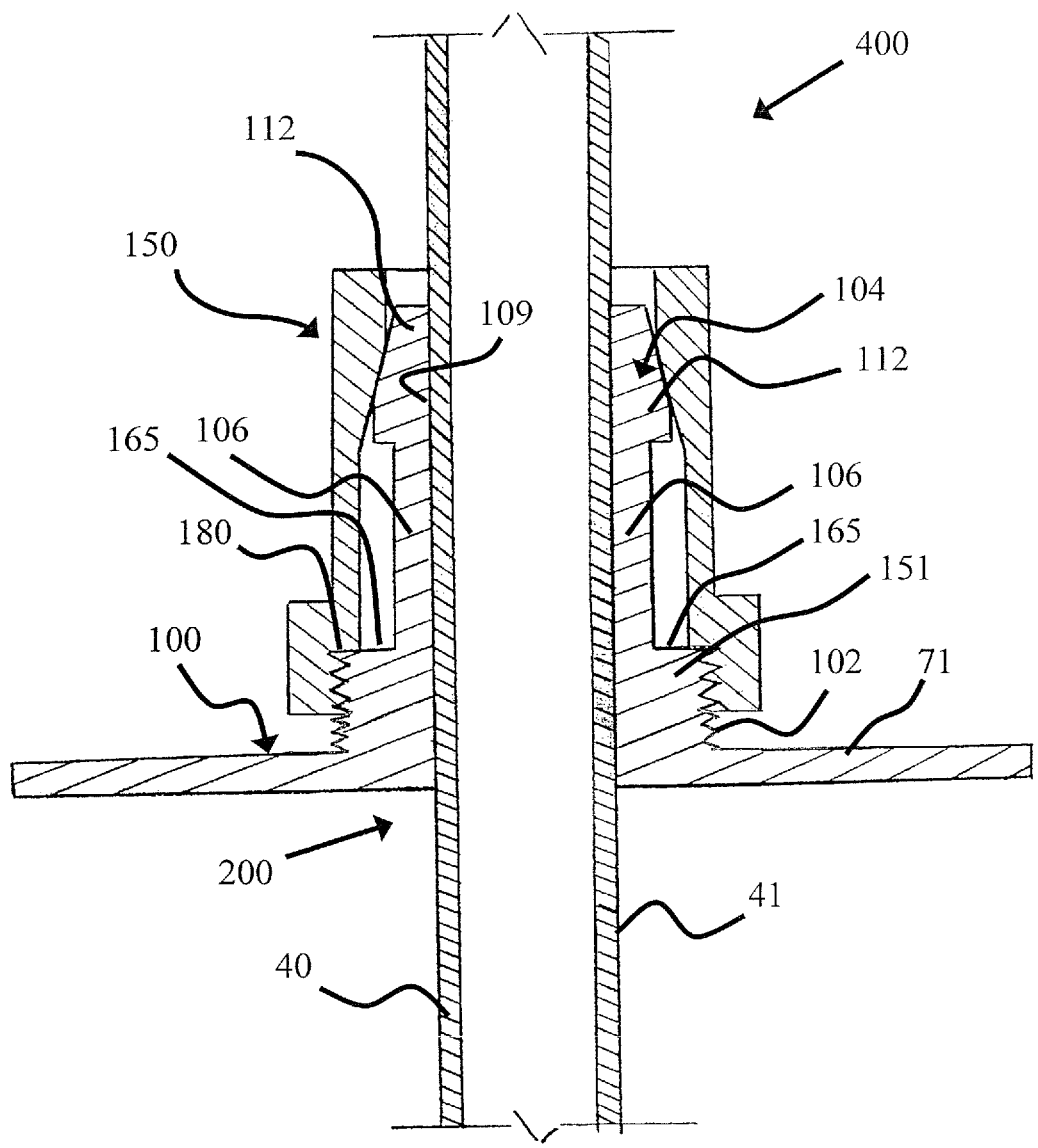
FIG. 22 is a cross-sectional, front elevation view of an alternative embodiment of the subject invention utilizing a compression mechanism.

FIG. 22 illustrates one example of a colletted external retaining member 100 engaged with an embodiment of a union nut 150. In this embodiment, a plate member 71 has an attached threaded column 102 circumscribing the channel 72, as shown, for example, in FIG. 25. The threaded column 102 can extend distally 400 from, and substantially perpendicular to, the plate member to any desired height. Ideally, the height of the threaded column 102 is sufficient to permit a union nut 150 to operably connect to the threaded column by being screwed on to it an adequate distance to press the collet against the tube shaft 40.

In a further embodiment, a collet 104 is fixedly attached to the distal end 400 of the threaded column 102. The collet, like the threaded column, can circumscribe the channel 72. In one embodiment, the collet and threaded column form a contiguous passage with the channel 72 for receiving a tube shaft, as shown, by way of example, in FIGS. 22 and 25. Ideally, the tube shaft can move within the channel relatively easily. In one embodiment, a collet 104 comprises two or more arm sections 106 separated by slots 108 that provide flexibility to the arm sections, thus permitting the arm sections 106 to be pushed together, so that at least a portion of the inside surface 109 of the collet 104 can make contact with and grip, by means of frictional force, a tube shaft 40 therein. FIG. 25 illustrates a cross-section of an embodiment of a collet having four arm sections, where two collets separated by a slot.

In a further embodiment, the outer surface 110 of the collet can be angled, so that it is formed into a wedge 112, where the distal end 400 is narrower than the proximal end 200. In one embodiment, the entire outer surface of the collet is formed into a wedge 112, such that each arm section 106 of the collet forms a part of the wedge. One example of this is shown in FIG. 25B.

Figure 25A:
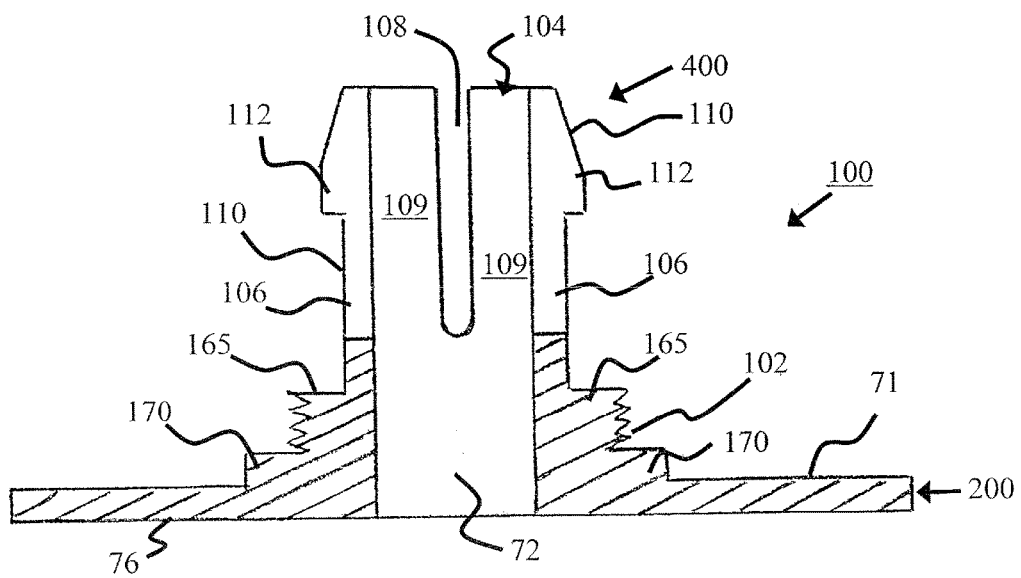
FIG. 25A is a cross-sectional, front elevation view of an embodiment of a colletted external retaining member, according to the subject invention, that can be operably connected to a union nut.
Figure 25B:
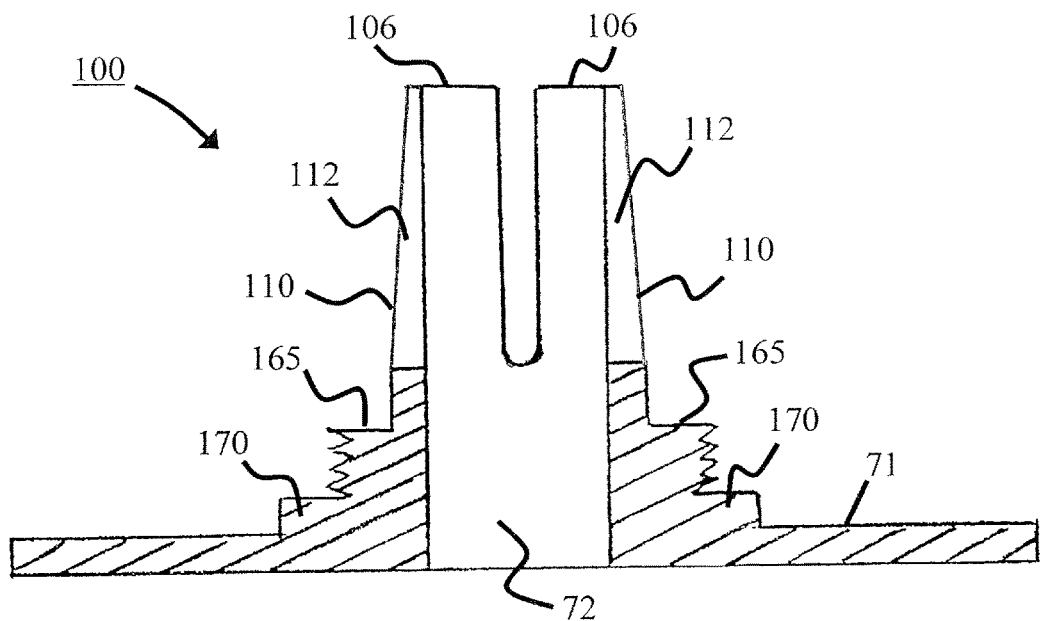
FIG. 25B is a cross-sectional, front elevation view of an alternative embodiment of a colletted external retaining member, according to the subject invention, that can be operably connected to a union nut.

In an alternative embodiment, a distal portion 400 of the outer surface 110 is formed into a wedge 112, such that a portion of the distal end of each section of the collet forms part of the wedge, an example of which is shown in FIG. 25A. Ideally, the dimensions and angle of the wedge 112 are coordinated with the height of the threaded column, and the union nut as described below, so that they can operate cooperatively to secure the collet against a tube shaft.

In a further embodiment, a female union nut 150 is configured to cooperatively receive and engage with the colletted retaining member 100. A union nut 150 can be, in general, a device for constricting the arm sections of the collet 104, so that they press against a tube shaft 40 creating sufficient frictional force, f, to secure the colletted external retaining member 100 in a desired position on the tube shaft 40.

Figure 24:
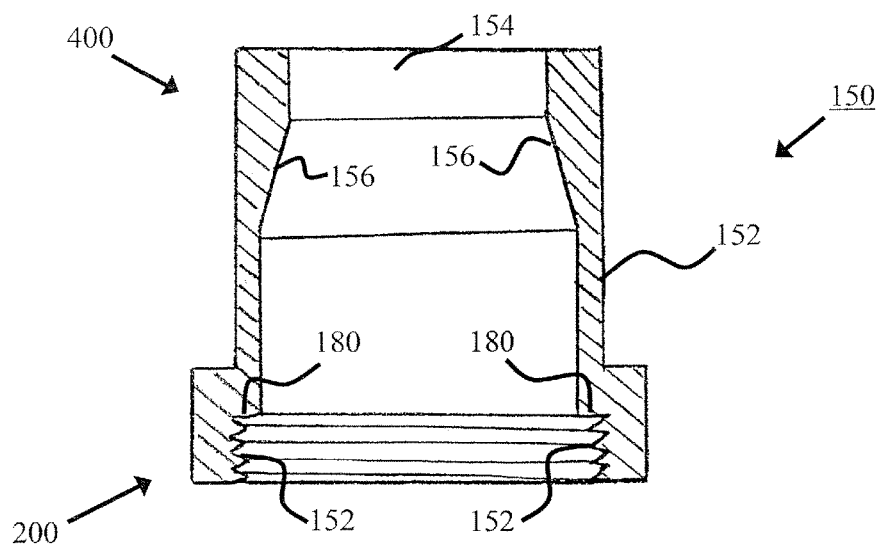
FIG. 24 is a cross-sectional, front elevation view of an embodiment of a union nut according to the subject invention.

In one embodiment, a union nut 150 comprises a sleeve body 152 having a bore 154 therethrough communicating a proximal end 200 with a distal end 400. In a further embodiment, the proximal end of the bore is configured with continuous threading 155. FIG. 24 illustrates one example of this embodiment. The continuous threading 155 in the union nut can be cooperatively engaged with the threaded column 102 on a colletted retaining member 100. It is recommended that the threaded column have a height adequate to allow a union nut suitable range of motion up and down the column.

In a still further embodiment, the distal end 400 of the bore is constricted so as to form an internal inclined plane 156 therein, such as shown, for example, in FIG. 24. The angle and direction of the internal inclined plane 156 can be approximately equivalent to the angle and direction of the wedge 112 on the collet. More specifically, the wedge 112 and the inclined plane 156 can be substantially parallel, as shown in the examples in FIGS. 24 and 25A. This can allow the inclined plane 156 to be seated and pressed against the wedge 112 of the collet, as shown, for example, in FIG. 22.

A gastrostomy feeding tube having a colletted retaining member 100 with a compatible union nut 150 thereon can be properly adjusted by 1) positioning the tube shaft 40 so that the internal retention member 20 is against the gastric wall 11 of a patient, 2) positioning the colletted retaining member 100 on the tube shaft so that the plate member 71 is against the skin 14 of the patient, in a position that will retain the internal member against the gastric wall 3) disposing the union nut 150 over the colletted retaining member 100, whereby the continuous threading 155 within the union nut can be engaged with the threaded column 102 on the colletted retaining member, 4) screwing the union nut onto the threaded column thereby causing the collet 104 to abut the internal inclined plane 156 of the union nut, and 5) continuing to screw the union nut onto the threaded column until the arm sections 106 of the collet 104 are pressed against the tube shaft sufficiently that the frictional force between the inside surface 109 of the collet and the exterior surface 41 of the tube shaft is adequate to maintain the position of the colletted retaining member 100.

Figure 26:
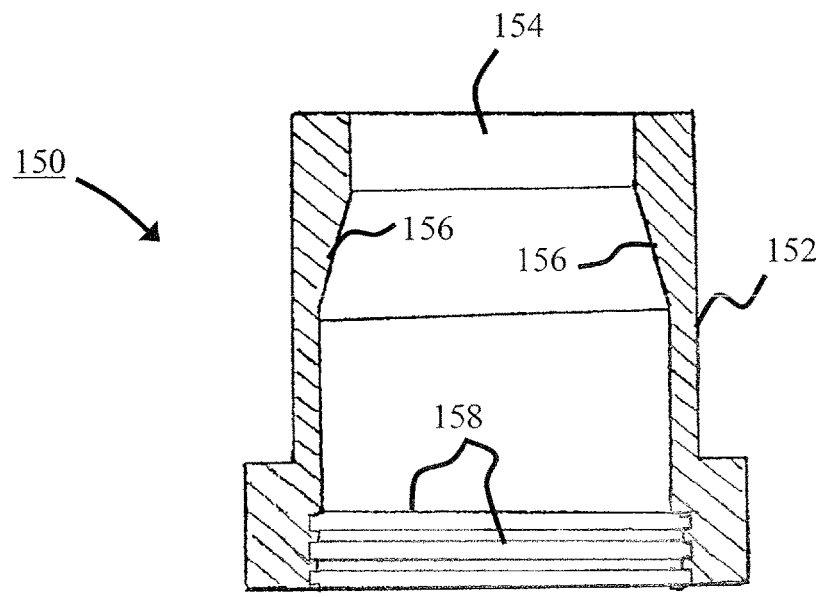
FIG. 26 is a cross-sectional, front elevation view of an alternative embodiment of a union nut, according to the subject invention, having one or more grooves.

Alternative embodiments of a collet and union nut can be engaged by securing elements and cooperating features that create a friction fit therebetween. In one embodiment, the proximal end 200 of a union nut can be configured with a plurality of internal grooves 158, as shown, for example, in FIG. 26. In a further alternative embodiment, the plate member 71 can have a friction column 160 extending distally from, and circumscribing the channel of, the external retaining member. The friction column can have a plurality of external surface features 162. Extended surface features 162 can include any of a variety of structures, including, but not limited to, ribs, nibs, rings, or other raised structures on the friction column. In a particular embodiment, an extended surface feature can be one or more teeth 50, such as described above.

With this embodiment, the union nut and friction column can be snap-fitted together by pushing the proximal end 200 of the union nut onto the friction column, so that one or more of the external surface features engage with one or more of the grooves. The union nut can be pushed onto the friction column until the internal inclined plane 156 presses against the wedge 112 portion to provide adequate frictional force against the tube shaft, as described above. If the position of the external retaining member or the tube shaft needs to be adjusted, the union nut can be pulled or pushed proximally or distally, respectively, to disengage with or engage with different, external surface features on the friction column.

It would be within the skill of a person trained in the art to devise alternative devices and methods by which a union nut could be engaged with a column on a plate member. Such alternatives which provide the same function, in substantially the same way, and provide substantially the same result are within the scope of the subject invention. Should a union nut be over-tightened on a collet, it can be difficult, or even impossible to release it without causing damage to the colletted retaining member, union nut, and/or the tube shaft. Extremely over-tightened collets can also potentially damage a gastrostomy device or render it inoperable if the inside surface 109 constricts the tube shaft too much. Advantageously, embodiments of the subject invention provide mechanisms that can prevent over-tightening of a union nut onto a collet.

In one embodiment, the height of the threaded column, or other type of collet fitting column, above the distal end of the plate member can be configured to provide adequate complementary attachment to a union nut, but cause the union nut to abut the distal side of the plate member before being over-tightened. In an alternative embodiment, the continuous threading 155 within the union nut can have limited range, such that it can only be tightened onto a threaded column to a prescribed distance, as shown, for example, in FIG. 22.

In yet another embodiment, a plate member 71 is configured with one or more stops 170 positioned around a column (threaded or friction) on the distal surface of the plate member 71. When engaged with a column, a union nut can abut against the one or more stops prior to being over-tightened. A stop can have any of a variety of configurations. In one embodiment, a stop is a raised area of the plate member, as shown, for example, in FIGS. 23, 25A, and 25B. A stop can fully circumscribe a column. Alternatively, a stop can comprise multiple members arranged around a column.

Ideally, the height of a stop coincides with the dimensions of the inclined plane 156 and the wedge 112, so that inhibition of the union nut by the stops does not prevent the collet from being sufficiently tightened to secure the position of an external retaining member. A person with skill in the art would be able to determine any of a variety of stop configurations that would prevent a union nut from being over-tightened on a collet. Such variations are within the scope of the present invention.

Figure 23:
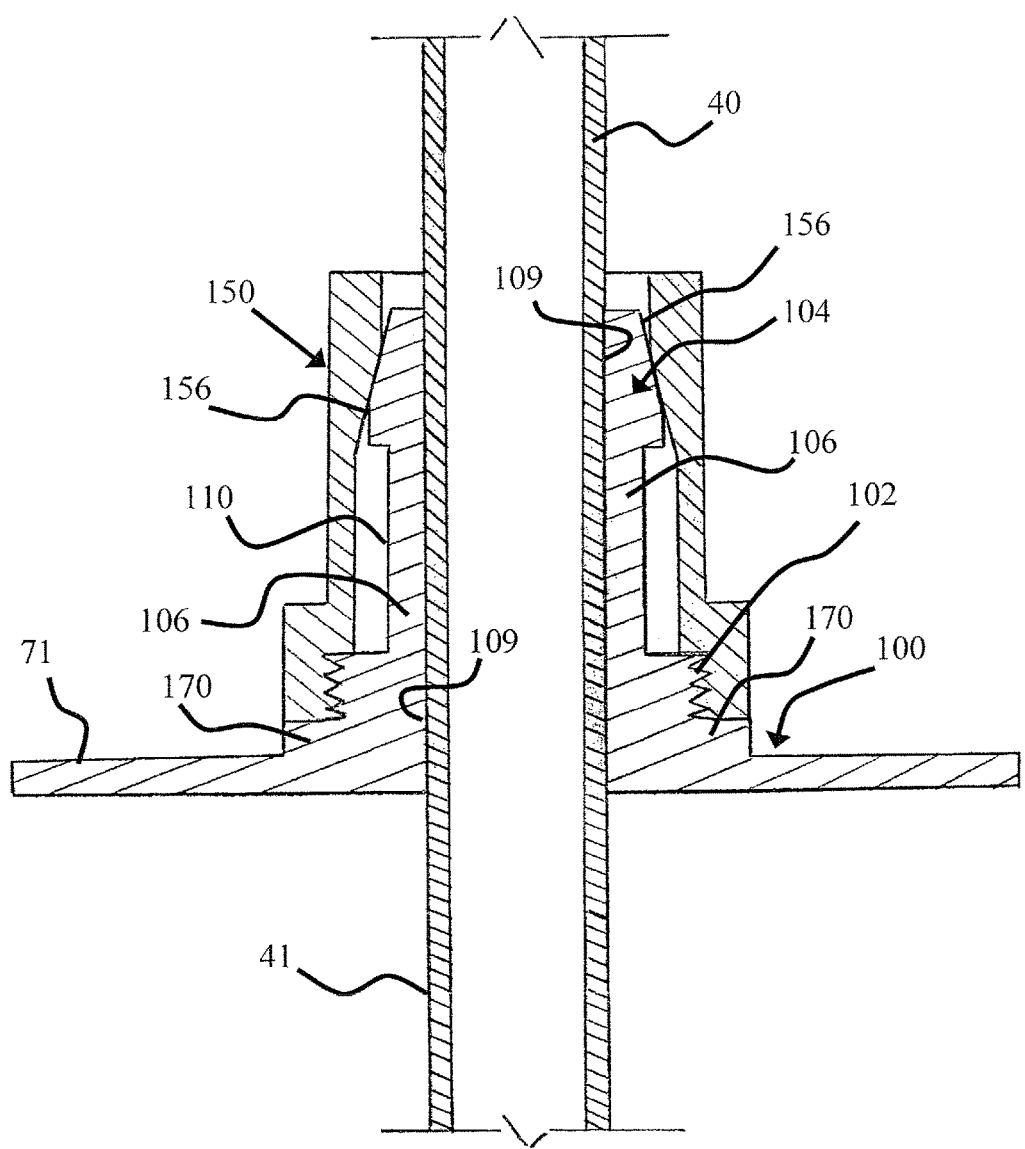
FIG. 23 is a cross-sectional, front elevation view of an alternative embodiment of the subject invention utilizing a compression mechanism to secure a position on a tube shaft. This embodiment includes a stop that prevents the compression mechanism from being over-tightened.
Figure 27:
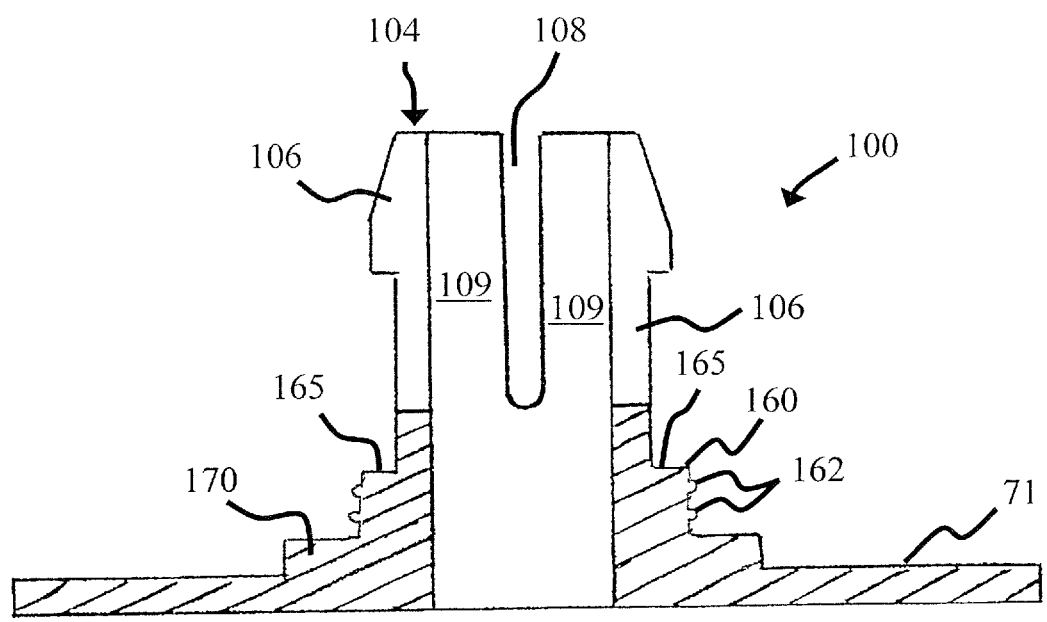
FIG. 27 is a cross-sectional, front elevation view of an alternative embodiment of a colletted external retaining member, according to the subject invention, that can be operably connected to a union nut by one or more ribs.

A union nut can also comprise an internal mechanism to prevent the inclined plane and wedge from being over-tightened. The internal mechanism in the union nut can be utilized alone or with one or more stops. In one embodiment, a union nut has an internal shoulder 180 proximal 200 to the inclined plane 156 and distal 400 to the continuous threading or grooves at the proximal end 200, one example of which is shown in FIG. 24. The internal shoulder can inhibit the column from being pushed or screwed too far into the channel 72, thus preventing the collet and inclined plane from being over-tightened. In one embodiment, the diameter of the internal shoulder 180 is smaller than the diameter of the continuous threads or grooves. In a further embodiment, the diameter of the collet is also smaller than the diameter of the continuous threading or grooves, thus forming a shelf 165 between the wedge 112 and the continuous threading or grooves. FIGS. 25A and 27 illustrate one example of this embodiment. This can allow the internal shoulder to overlap the distal end of the continuous threading or grooves, effectively preventing any further movement, or over-tightening, of a column distal to the internal shoulder when it abuts the shelf. FIG. 22 illustrates an example of this embodiment wherein a threaded column is prevented from being fully screwed into a union nut by means of the internal shoulder against the shelf. FIG. 23 illustrates an embodiment where an internal shoulder 180 and shelf 165 are utilized cooperatively with a stop 170.

One advantage of the collet fitting arrangement is that the moving components, i.e., the collet fitting components, do not make contact with the skin of a patient. This can be more comfortable for a patient because the colletted external retaining member can be adjusted without turning the plate member against the skin, causing uncomfortable friction around the stoma. This can also ensure that patient movements do not unwittingly loosen the collet fitting. A further advantage is that the colletted retaining member can be adjusted without having to insert the hand or another device between the skin and the plate, as is typically done with currently known devices. In fact, with the embodiments of the subject invention, the diameter of the channel 72 can be large enough to provide easy movement of the colletted retaining member up and down the tube shaft, since it can be held in place by the union nut and collet, rather than frictional forces between the channel and tube shaft exterior 41.

Thus, an advantage of the embodiments of the subject invention is the ability to adjust the external retaining member by pushing, pulling, or screwing it proximally or distally on a tube shaft. There are other known devices that utilize an external retaining member that can be twisted or turned, e.g., screwed, onto a tube shaft, so as to increase pressure of the internal retention member against the gastric wall. However, as the external retaining member comes into contact with the skin and stoma site, it can be difficult or uncomfortable to tighten, by turning or screwing, the external retaining member sufficiently to inhibit leaking. The external retaining member embodiments of the subject invention can be more comfortably adjusted and can, thus, apply greater and/or more consistent pressure against the internal retention member to better inhibit leaking.

Current practice when installing a gastric feeding tube into a patient is to employ sutures to hold an external retaining member in place against the skin. The external retaining member of most gastric feeding tube devices includes suture holes by which the external retaining member can be sutured to the skin. This is typically required for currently known friction fit devices and those which are tightened by screwing them against the skin and onto a feeding tube. As an individual moves, it is possible for a weak frictional fit to become loosened or for threaded external retaining members to become unscrewed or screwed too tightly onto a tube shaft. Sutures are required to inhibit movement of the external retaining member. However, in order to make adjustments to such devices, the sutures usually have to be removed, so that the external retaining member can be screwed, or unscrewed, as is necessary.

A further advantage of the embodiments of the subject invention is that sutures can still be employed to secure an external retaining member, but they are not required. In one embodiment, at least one suture hole 87 is disposed through an external retaining member, an example of which is shown in FIGS. 11 and 12. The external retaining member embodiments of the subject invention are typically not subject to the normal movements of an individual and are not prone to incidental loosening. Also, the method of adjusting the external retaining member does not require turning it relative to the skin, but by moving it proximally or distally relative to the tube shaft. Further embodiments of external retaining members that can be operatively engaged to inhibit rotation of a tube shaft have been disclosed above. Therefore, if sutures are utilized, they can remain in place even if the external retaining members must be adjusted.

Because the external retaining members of the subject invention can be pressed tighter against the skin, it can be important to inhibit tissue ischemia. Therefore it is important that the embodiments of the subject invention not be adjusted too forcefully. To further inhibit tissue ischemia, the external retaining members can include one or more ergonomic features 88 that contact the skin. In one embodiment, an external retaining member 70 or 100 has a bottom side 76 that is modified with a shape or structures that reduce or prevent tissue ischemia. In one embodiment, an external retaining member has an uneven bottom side 76 so that pressure applied to tissue is uneven or variable, but is still capable of providing sufficient consistent pressure to prevent leakage. By way of non-limiting example, ergonomic features can include a bottom side that is wavy or curved or, alternatively, that has multiple ridges, ribs, tabs, or other structures that protrude from the proximal surface. In other words, the bottom side can be modified to be other than a substantially flat surface. FIG. 17 illustrates an alternative embodiment with multiple tabs protruding from the bottom side. The tabs essentially break up the planar bottom side, so that uneven or variable pressure is applied to the skin, which can inhibit tissue ischemia.

The size of the ergonomic features can vary according to various factors known to those with skill in the art. In one embodiment, the ergonomic features protrude from the bottom surface 76 or proximal side 200 between approximately 2.0 mm and approximately 5.0 mm. In a particular embodiment, the ergonomic structures protrude from the bottom surface 76 or proximal side 200 between approximately 2.5 mm and approximately 3.5 mm. In a specific embodiment, the ergonomic structures protrude from the bottom surface 76 or proximal side 200 approximately 3.0 mm.

Finally, the factors that can be considered by those skilled in the art with regard to the choice of materials for each of the components of the subject invention have been discussed above. But, it is worth repeating and should be understood that a person skilled in the art would be able to determine a variety of materials that would be appropriate for one or more of the components described for the embodiments of the subject invention. While gastric feeding tubes are generally manufactured from biocompatible materials, there are a variety of such materials that can be utilized. Silicone is one example of a biocompatible material often utilized for gastric feeding tubes. However, because of the interaction of the one or more teeth 50 attached to certain embodiments of a gastric tube shaft of the subject invention and certain embodiments of external retaining members of the subject invention, it may be more appropriate to use other biocompatible materials instead of, or in addition to, silicone. It should be understood that such variations in the utilization of materials that provide the same function, in substantially the same way, providing substantially the same result are within the scope of the subject invention.

Following is an example that illustrates a procedure for practicing the subject invention. This example is provided for the purpose of illustration only and should not be construed as limiting. Thus, any and all variations that become evident as a result of the teachings herein or from the following example are contemplated to be within the scope of the present invention.

Figure 28:
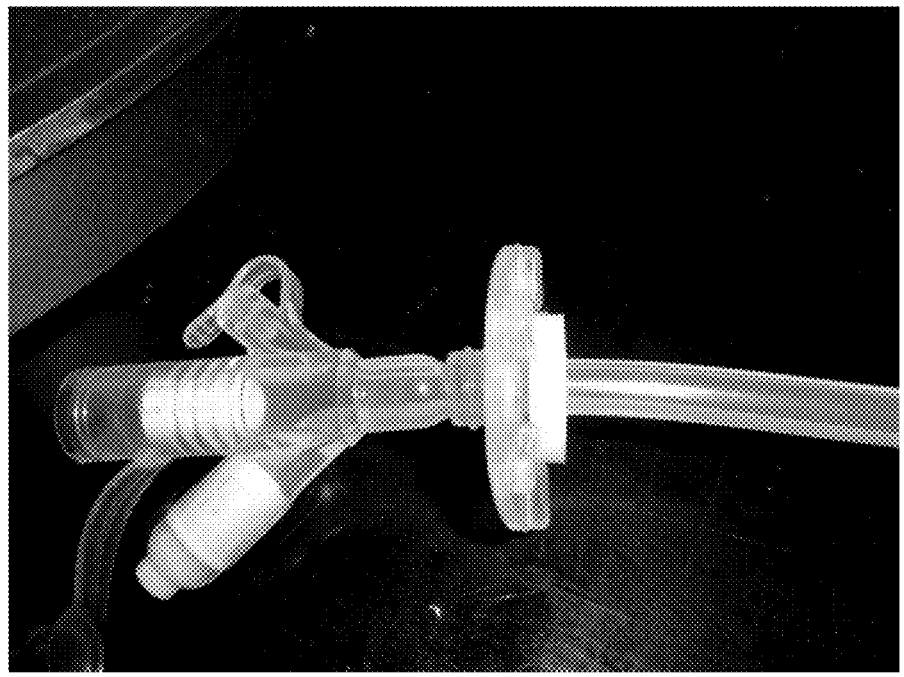
FIG. 28 (prior art) is a photograph of the externally located end of a typical gastrostomy feeding tube that is adjusted with a flange that slides along the length of the tube and is maintained in position by frictional force between the flange and the tube.

Example: Comparison of a Standard Gastrostomy Feeding Tube (G-Tube) Flange and a Flange Utilizing a Collet Fitting A standard G-tube, such as the Kimberly-Clark Gastrostomy Feeding Tube, has a 24 Fr diameter silicone tube with a silicone flange circumscribing the tube. An example of this type of feeding tube is shown in FIG. 28. The flange on a feeding tube is used to prevent the tube from moving after installation by positioning the flange, by hand, against the patient's skin and setting the desired force or pressure required to maintain an internal retaining member, such as a bumper or balloon, against the fistula. However, in some cases, the flange can slip or slide on the tube and move away from the skin, reducing pressure, and causing the internal retaining member to move away from the fistula. The position of a standard feeding tube flange on a feeding tube is maintained by frictional forces and has no mechanism to adjust the frictional force on the tube.

Figure 29:
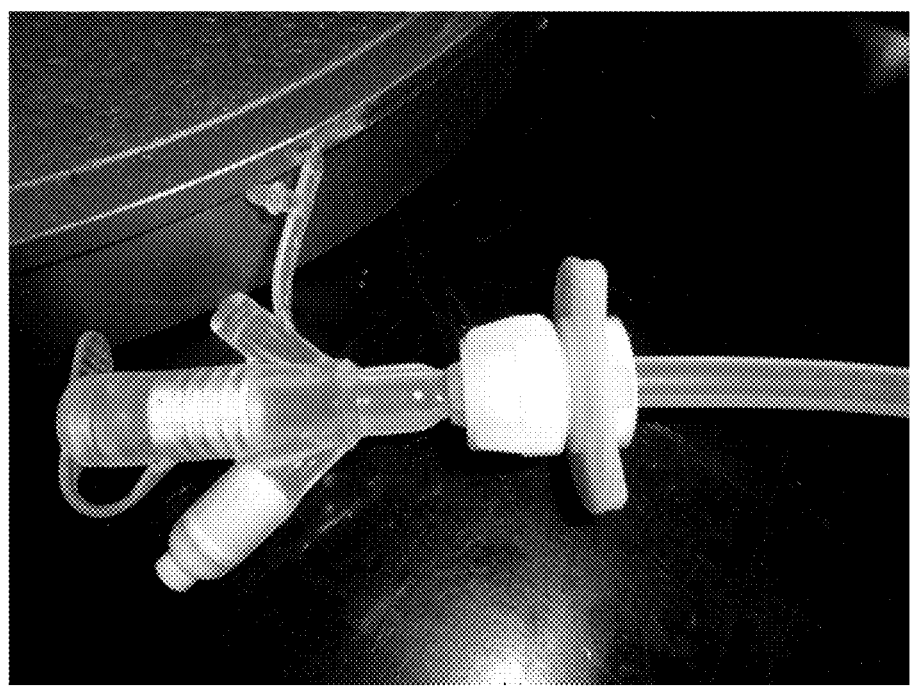
FIG. 29 is a photograph showing a embodiment of the subject invention utilizing a union nut with a colletted external retaining member, which are designed to prevent movement of flange on the tube.

The collet flange is designed to inhibit movement of the flange on the tube by using a colletted sleeve with a compression nut. FIG. 29 illustrates one example of this embodiment. The flange nut center section, which fits around the tube, has several arm sections around the perimeter with slots between them to allow the arm sections to be compressed against the tube. A nut is threaded over this center section and compresses the center section against the tube when tightened.

Figure 30:
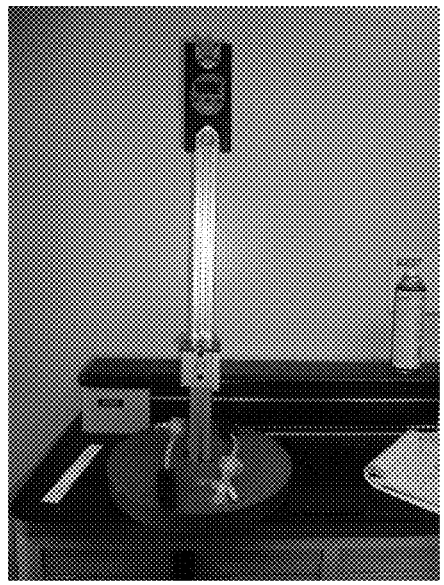
FIG. 30 is a photograph showing the vertical stand and hanging scale arrangement used to measure the force required to slide the flange along the tube, as described in the Example.

A comparison between a standard flange and the collet flange was conducted to determine which flange provides more clamping force on the tube. A vertical stand was used with a hanging scale to measure the force required to slide a flange along the tube. The scale used was an American weight scale model TL-330. (See FIG. 30) The scale could measure in pounds, ounces, or kilograms and was set to measure in ounces. The digital display on the scale was set to display and hold the maximum force achieved when a flange was moved along the tube.

Figure 31:
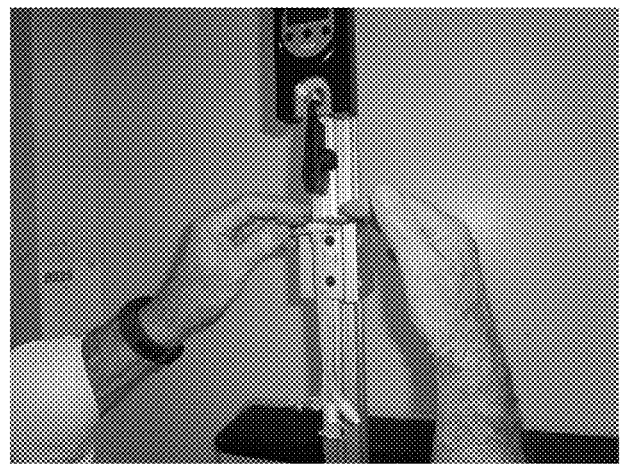
FIG. 31 is a photograph showing the process by which gastrostomy tubes were tested by being clamped to the stand and scale configuration shown in FIG. 30. Both a standard gastrostomy tube and a gastrostomy tube with a collet fitting, according to the subject invention, were tested as described in the Example.
Figure 32:
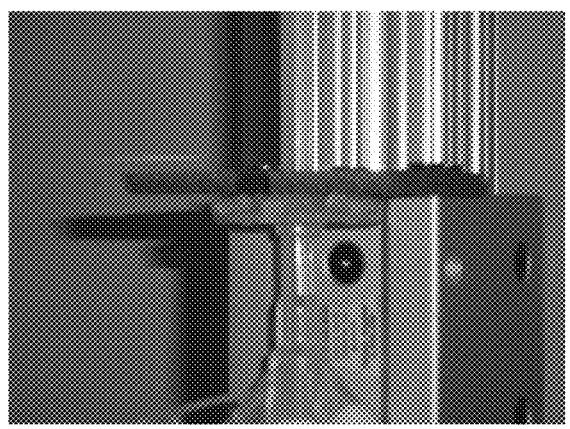
FIG. 32 is a photograph showing a nylon washer that was used to assist in moving the flanges along the length of the tube. As described in the Example, the flange of the standard gastrostomy tube tended to fold or bend during testing. The nylon washer was employed to reduce this effect and, for consistency, was utilized when testing the collet fitting embodiment as well.

Two tubes, one with a standard feeding tube flange and one with the collet flange were separately clamped to the scale. Their flanges were moved by hand to slide downward along the tube at a constant rate and the applied force was recorded by the scale. (See FIG. 31) Ten readings were recorded and averaged for each flange. The results of the test are provided in Table 1, below. It can be deduced from the data shown in Table 1 that the amount of force necessary to move the standard flange was 18 ounces and the force necessary to move the collet flange was 46 ounces. These results indicate that the force required to move the collet flange is approximately 2.5 times greater than the force required to move the standard flange. Stated another way, frictional force between the collet flange and the tube is increased by 250% over the standard friction fit flange.

It should be noted that when the standard flange, which comprised silicone, was pushed along the tube by hand, the standard flange tended to bend or fold over making it difficult to slide it along the tube. To eliminate this problem a nylon washer was placed on the flange around the tube. The nylon washer distributed force evenly and inhibited the folding or bending problem. The inside diameter of the washer was larger than the tube so that it did not impact the measurement of the clamping force of the flange on the tube. Although it was not necessary, a similar washer was used on the collet flange, so that the test conditions would be the same for both flanges.

This test was conducted using a dry tube, that is, no liquid or lubricant was applied. In order to simulate a situation where the tube would be wet, WD-40 lubricant was applied to both tubes. After wiping the excess lubricant from the tube, the tests were repeated on the lubricated tubes.

In conclusion, this test showed that the collet flange provided more clamping force than a standard flange by a factor of 2.5:1. In addition, the clamping force of the collet flange nut can be increased or decreased by redesigning with smaller or larger inside diameters and slots.

TABLE 1

| Force to Move Flange (in Ounces) | | | | | |
|---|---|---|---|---|---|
| Dry Tube | | Dry Tube Switching tube | | Tubes with WD-40 | |
| Standard | G/H | Standard | G/H | Standard | G/H |
| 18 | 42 | 14 | 56 | 25 | 32 |
| 11 | 53 | 14 | 46 | 21 | 42 |
| 18 | 39 | 7 | 48 | 14 | 35 |
| 18 | 46 | 11 | 46 | 18 | 39 |
| 21 | 46 | 14 | 46 | 16 | 42 |
| 18 | 46 | 18 | 49 | 18 | 39 |
| 14 | 46 | 18 | 53 | 21 | 42 |
| 18 | 49 | 18 | 43 | 19 | 42 |
| 18 | 46 | 21 | 48 | 18 | 39 |
| 21 | 46 | 14 | 49 | 16 | 40 |
| Avg: 18 | Avg: 46 | Avg: 15 | Avg: 48 | Avg: 19 | Avg: 39 |

G/H = 2.5:1
Standard

The scope of the invention is not limited by the specific examples and suggested procedures and uses related herein since modifications can be made within such scope from the information provided by this specification to those skilled in the art.

The examples and embodiments described herein are for illustrative purposes only and various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and various modifications, both as to equipment details and operating procedures, can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

We claim:

1. A gastric feeding tube comprising:
   a tube shaft with a proximal end and a distal end;
   a colletted external retaining member comprising:
      a column, with one or more securing elements, circumscribing a channel,
      a collet having at least two arm sections with slots therebetween and fixedly attached to a distal end of the column, wherein at least a portion of the collet comprises a wedge-shaped outer surface and an inside surface,
   wherein the collet forms a continuous passage with the channel for movably receiving the tube shaft therethrough; and
   a union nut comprising:
      a sleeve body with a bore therethrough that communicates a proximal end of the union nut with a distal end of the union nut and moveably receives the tube shaft such that the union nut is distal to the colletted external retaining member and the tube shaft passes through the distal end of the bore,
      an internal inclined plane at or near the distal end of the bore, and
      one or more cooperating features within the proximal end of the bore, which are compatible with the one or more securing elements on the column of the colletted external retaining member;
   such that when the union nut is cooperatively engaged with the colletted external retaining member, the inclined plane within the union nut seats or presses against at least a portion of the wedge-shaped collet as the securing elements on the column engage with the cooperating features in the union nut, which causes the inside surface of the arm sections of the collet to be pressed against the tube shaft in the continuous-passage and secure the position of the colletted external retaining member on the tube shaft extending from the bore of the sleeve body and wherein removal of the union nut from the colletted external retaining member releases the inside surface pressed against the tube shaft and allows the colletted external retaining member to move freely along the tube shaft.

2. A gastric feeding tube according to claim 1, wherein the securing element and compatible feature comprise compatible continuous threading.

3. A gastric feeding tube according to claim 2, further comprising a stop on the threaded column against which the union nut can abut to inhibit over-tightening.

4. A gastric feeding tube according to claim 2, further comprising:
   an internal shoulder within the bore of the union nut and distal to the continuous threading, and
   a shelf on the colletted external retaining member and distal to the threaded column, such that when the union nut is cooperatively engaged with the colletted external retaining member, the internal shoulder can abut the shelf to inhibit further movement of the threaded column within the bore.

5. A gastric feeding tube according to claim 1, wherein the securing element comprises one or more external surface features and the compatible features comprise one or more grooves.

6. A gastric feeding tube according to claim 1, wherein the frictional force between the colletted external retaining member is approximately 250% greater than the frictional force of a friction fit external retaining member.

7. A gastric feeding tube according to claim 1, wherein the collet further comprises at least four arm sections.

8. A gastric feeding tube according to claim 1, wherein the collet further comprises at least three arm sections.

9. A gastric feeding tube according to claim 1, further comprising a plate-member with a proximal side and a distal side with a channel therethrough that is continuous with the channel in the column.

10. A gastric feeding tube according to claim 1, wherein the wedge-shape of the collet extends along the entire length of the arm sections.

11. A method for installing a gastric feeding tube, in a patient in need treatment, comprising:
   obtaining a gastric feeding tube comprising:
   a tube shaft with a proximal end having a retention member thereon and a distal end;
   a colletted external retaining member comprising:
      a column, with one or more securing elements, circumscribing a channel,
      a collet having at least two arm sections with slots therebetween and fixedly attached to a distal end of the column, wherein at least a portion of the collet comprises a wedge-shaped outer surface and an inner surface,
   wherein the collet forms a continuous passage with the channel for movably receiving the tube shaft therethrough and
   a union nut comprising:
      a sleeve body with a bore therethrough that communicates a proximal end of the union nut with a distal end of the union nut and moveably receives the tube shaft such that the union nut is distal to the colletted external retaining member and the tube shaft passes through the distal end of the bore, an internal inclined plane at or near the distal end of the bore, and one or more cooperating features within the proximal end of the bore, which are compatible with the one or more securing elements;

the method comprising, installing the gastric feeding tube with the tube shaft disposed through a fistula in a patient and the proximal end and retention member located in the gastric lumen of a patient;

adjusting the tube shaft in the fistula until the retention member is against the fistula;

inserting the distal end of the tube shaft into the continuous passage of the collet;

advancing the external colletted retaining member on the tube shaft towards the patient until the proximal side is pressed against the patient;

advancing the union nut towards the colletted external retaining member so that the internal inclined plane in the bore engages with the wedge-shaped outer surface of the collet to press the at least two arm sections against the tube shaft to secure the position of the colletted external retaining member on the tube shaft and so that the tube shaft extends distally out of the bore of the sleeve body.

12. A method according to claim 11, wherein the securing element is at least one of continuous threading and external surface features and the compatible feature is at least one of continuous threading and one or more internal grooves.

13. A method according to claim 12, further comprising:

disengaging the union nut from the column on the colletted external retaining member so that the inside surface is released from around the tube shaft;

adjusting the tube shaft in the fistula;

adjusting the external colletted retaining member on the tube shaft; and re-engaging the union nut with the column to press the inside surface of the collet arms against the tube shaft and secure the adjusted position of the colletted external retaining member on the tube shall.

14. A method according to claim 11, further comprising a plate member on the external retaining member, the plate member comprising a proximal side, a distal side, and a channel therethrough that is continuous with the channel in the column, where the method further comprises advancing the collected retaining member on the tube shaft towards the patient until the proximal side of the plate member is pressed against the patient.

* * * * *